United States Patent
Benbow

(10) Patent No.: US 7,709,473 B2
(45) Date of Patent: May 4, 2010

(54) SUBSTITUTED 2H-[1,2,4]TRIAZOLO[4,3-A]PYRAZINES AS GSK-3 INHIBITORS

(75) Inventor: John William Benbow, Norwich, CT (US)

(73) Assignee: Pfizer Inc., New York, NY (US)

( * ) Notice: Subject to any disclaimer, the term of this patent is extended or adjusted under 35 U.S.C. 154(b) by 132 days.

(21) Appl. No.: 10/575,395

(22) PCT Filed: Sep. 27, 2004

(86) PCT No.: PCT/IB2004/003137

§ 371 (c)(1),
(2), (4) Date: Mar. 13, 2007

(87) PCT Pub. No.: WO2005/035532

PCT Pub. Date: Apr. 21, 2005

(65) Prior Publication Data

US 2007/0249612 A1    Oct. 25, 2007

(51) Int. Cl.
| A61K 31/54 | (2006.01) |
| A61K 31/535 | (2006.01) |
| A61K 31/497 | (2006.01) |
| A61K 31/505 | (2006.01) |
| C07D 417/00 | (2006.01) |
| C07D 413/00 | (2006.01) |
| C07D 403/00 | (2006.01) |
| C07D 239/02 | (2006.01) |

(52) U.S. Cl. .................. 514/227.8; 544/60; 544/122; 544/295; 544/329; 544/330; 514/235.5; 514/252.14; 514/275

(58) Field of Classification Search .......... None
See application file for complete search history.

(56) References Cited

FOREIGN PATENT DOCUMENTS

| FR | 2662163 | 5/1990 |
| GB | 1235910 | 6/1971 |
| WO | WO2004085439 | 10/2004 |

OTHER PUBLICATIONS

Mallett et. al. Journal of the Chemical Society [Section] C: Organic (1966), (22), 2038-43.*
Dorwald F. A. Side Reactions in Organic Synthesis, 2005, Wiley: VCH, Weinheim p. IX of Preface.*
Sarges, et. al., J. Med. Chem., 1990, 33(8), 2240-54.*
Wolff et. al., "Burger's Medicinal Chemistry and Drug Discovery," 5th Ed. Part 1, pp. 975-977 (1995).*
Banker, et. al., Modern Pharmaceuticals, 1996, p. 596.*

* cited by examiner

*Primary Examiner*—James O Wilson
*Assistant Examiner*—Jeffrey H Murray
(74) *Attorney, Agent, or Firm*—Gregg C. Benson; John A. Wichtowski

(57) ABSTRACT

The invention relates to compounds of formula (I) prodrugs thereof, and the pharmaceutically acceptable salts of the compounds and prodrugs, wherein $R^a$, $R^b$, $R^1$ and $R^2$ are as defined herein; pharmaceutical compositions thereof; and uses thereof.

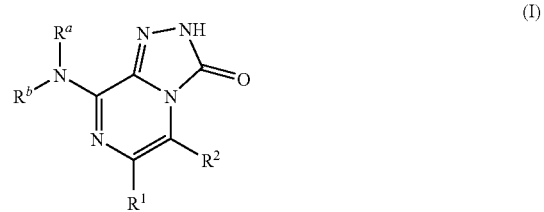

(I)

5 Claims, No Drawings

SUBSTITUTED 2H-[1,2,4]TRIAZOLO[4,3-A]PYRAZINES AS GSK-3 INHIBITORS

FIELD OF THE INVENTION

The invention relates to certain 2H-[1,2,4]triazolo[4,3-a]pyrazine-1-ones which are inhibitors of glycogen synthase kinase 3 (GSK-3) and, as such, are useful in the treatment of, inter alia, conditions, diseases, and symptoms such as diabetes, dementia, Alzheimer's Disease, bipolar disorder, stroke, schizophrenia, depression, hair loss, cancer, and the like.

BACKGROUND OF THE INVENTION

Glycogen synthase kinase-3 (GSK-3), a proline-directed, serine/threonine kinase for which two isoforms, GSK-3α and GSK-3β, have been identified, phosphorylates the rate-limiting enzyme of glycogen synthesis, glycogen synthase (GS). See, for example, Embi, et al., Eur. J. Biochem., 107, 519-527 (1980). GSK-3α and GSK-3β are both highly expressed in the body. See, for example, Woodgett, et al., EMBO, 9, 2431-2438 (1990) and Loy, et al., J. Peptide Res., 54, 85-91 (1999). Besides GS, a number of other GSK-3 substrates have been identified, including many metabolic, signaling, and structural proteins. Notable among the plurality of signaling proteins regulated by GSK-3 are many transcription factors, including activator protein-1; cyclic AMP response element binding protein (CREB); the nuclear factor (NF) of activated T-cells; heat shock factor-1; β-catenin; c-Jun; c-Myc; c-Myb; and NF-$_{KB}$. See, for example, C. A. Grimes, et al., Prog. Neurobiol., 65, 391-426 (2001), H. Eldar-Finkelman, Trends in Molecular Medicine, 8, 126-132 (2002), and P. Cohen, et al., Nature, 2, 1-8, (2001). Accordingly, targeting the activity of GSK-3 has significant therapeutic potential in the treatment of many disparate pathologies and conditions, for example, Alzheimer's Disease (A. Castro, et al., Exp. Opin. Ther. Pat., 10, 1519-1527 (2000)); asthma (P. J. Barnes, Ann. Rev. Pharmacol. Toxicol., 42, 81-98 (2002)); cancer (Beals, et al., Science, 275, 1930-1933 (1997), L. Kim, et al., Curr. Opin. Genet. Dev., 10, 508-514 (2000), and Q. Eastman, et al., Curr. Opin. Cell Biol., 11, 233 (1999)); diabetes and its related sequelae, for example, Syndrome X and obesity (S. E. Nikoulina, et al., Diabetes, 51, 2190-2198 (2002), Orena, et al., JBC, hair loss (S. E. Millar, et al., Dev. Biol., 207, 133-149 (1999) and E. Fuchs, et al., Dev. Cell, 1, 13-25 (2001)); inflammation (P. Cohen, Eur. J. Biochem., 268, 5001-5010 (2001)); mood disorders, such as depression (A. Adnan, et al., Chem. Rev., 101, 2527-2540 (2001) and R. S. B. Williams, et al., Trends Phamacol. Sci., 21, 61-64 (2000)); neuronal cell death and stroke (D. A. E. Cross, et al., J. Neurochem., 77, 94-102 (2001) and C. Sasaki, et al., Neurol. Res., 23, 588-592 (2001)); bipolar disorder (Klein, et al., PNAS, 93, 8455-8459 (1996)); skeletal muscle atrophy (G. J. Brunn, et al., Science, 277, 99-101 (1997), R. E. Rhoads, J. Biol. Chem., 274, 30337-30340 (1999), V. R. Dharmesh, et al., Am. J. Physiol. Cell Physiol. 283, C545-551 (2002), and K. Baar, et al., A. J. Physiol., 276, C120-C127 (1999)); decreased sperm motility (Vijayaraghavan, et al., Biol. Reproduction, 54, 709-718 (1996)); and in cardio-protection (C. Badorff, et al., J. Clin. Invest., 109, 373-381 (2002), S. Haq, et al., J. Cell Biol., 151, 117-129 (2000), and H. Tong, et al., Circulation Res., 90, 377-379 (2002)).

SUMMARY OF THE INVENTION

The invention relates to compounds of formula (I)

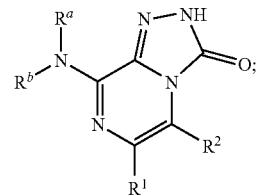

(I)

prodrugs thereof, and the pharmaceutically acceptable salts of the compounds and prodrugs, wherein $R^a$, $R^b$, $R^1$, and $R^2$ are as defined herein; pharmaceutical compositions thereof; and uses thereof.

DETAILED DESCRIPTION OF THE INVENTION

The present invention provides compounds of formula (I)

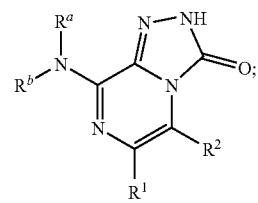

(I)

the prodrugs thereof, and the pharmaceutically acceptable salts of the compounds and prodrugs, wherein:

$R^a$ and $R^b$ are, independently:
(1) hydrogen;
(2) acetyl;
(3) —($C_1$-$C_6$)alkyl, optionally, and independently, substituted with from one to three:
(A) cyano; (B) halogen; (C) —$NR^3R^4$; (D) —$COR^5$; (E) —$OR^6$; (F) —$SR^6$; (G) —S(O)$R^6$; (H) —$SO_2R^6$; (I) aryl, optionally substituted independently with from one to three halogen; nitro; —$SO_2NH_2$; —($C_1$-$C_6$)alkyl; methylenedioxy; —$COR^5$; or —$OR^6$; (J) heteroaryl, optionally substituted independently with from one to three hydroxy; nitro; halogen; —$OR^6$; aryl, optionally substituted independently with —($C_1$-$C_6$)alkyl; heteroaryl; trifluoromethyl; or —($C_1$-$C_6$)alkyl, optionally substituted with hydroxy; (K) —($C_3C_{11}$) cycloalkyl, optionally substituted independently with from one to three cyano; —$COR^5$; or —$CH_2NR^3R^4$; or (L) —($C_3$-$C_{11}$)heterocycloalkyl, optionally substituted independently with from one to three —($C_1$-$C_6$)alkyl, optionally substituted with aryl; —$COR^5$; aryl, optionally substituted independently with halogen; oxo; or —($C_1$-$C_6$)alkoxy; wherein:

$R^3$ and $R^4$ are independently:
(a) hydrogen; (b) —$SO_2R^6$; (c) aryl, optionally substituted independently with from one to three halogen; cyano; nitro; —($C_1$-$C_6$)alkyl, —($C_1$-$C_6$)alkoxy, or —$COR^5$; (d) —($C_1$-$C_6$) alkyl, optionally substituted independently with from one to three —($C_3$-$C_{11}$)heterocycloalkyl; —($C_3$-$C_{11}$)cycloalkyl; —($C_1$-$C_6$)alkoxy; aryl; or heteroaryl; (e) heteroaryl, optionally substituted independently with from one to three halogen; trifluoromethyl; cyano; nitro; —$COR^5$; —($C_1$-$C_6$)alkyl, optionally substituted with —($C_3$-$C_{11}$)heterocycloalkyl; or —(C$_1$-C$_6$)alkoxy; (f) —(C$_1$-C$_{11}$)heterocycloalkyl, optionally substituted independently with from one to three —(C$_1$-C$_6$) alkyl; or (g) —COR$^5$; or R$^3$ and R$^4$, taken together with the nitrogen atom to which they are attached, form a 5- or 6-membered heterocycloalkyl ring, optionally having from one to three additional heteroatoms independently selected from nitrogen, oxygen, and sulfur, wherein said 5- or 6-membered heterocycloalkyl ring is optionally substituted independently with from one to three —(C$_1$-C$_6$)alkyl, optionally substituted with aryl;

R$^5$ is (h) hydroxy; (i) —(C$_1$-C$_6$)alkyl, optionally substituted independently with from one to three —CO$_2$H; —(C$_1$-C$_6$)alkoxy; or aryl; (j) —(C$_1$-C$_6$)alkoxy; (k) aryl, optionally substituted with halogen; (l) heteroaryl; or (m) —(C$_3$-C$_{11}$) heterocycloalkyl, optionally substituted independently with from one to three oxo; —CO$_2$H; or —(C$_1$-C$_6$)alkyl; and R$^6$ is (n) hydrogen; (o) —(C$_1$-C$_6$)alkyl, optionally substituted independently with from one to three hydroxy; —(C$_1$-C$_6$)alkoxy; aryl, optionally substituted with halogen; or heteroaryl, optionally substituted with —CH$_2$NR$^3$R$^4$; (p) aryl, optionally substituted independently with from one to three halogen; —(C$_1$-C$_6$)alkyl; cyano; trifluoromethyl; or —OR$^6$; (q) heteroaryl, optionally substituted independently with from one to three amino; —(C$_1$-C$_6$)alkyl; —(C$_1$-C$_6$)alkoxy; or —COR$^5$; or (r) —(C$_3$-C$_{11}$)heterocycloalkyl, optionally substituted independently with from one to three —(C$_1$-C$_6$) alkyl;

(4) —(C$_3$-C$_{11}$)cycloalkyl; or (5) —(C$_3$-C$_{11}$)heterocycloalkyl, optionally substituted independently with from one to three halogen; —COR$^5$; —(C$_1$-C$_6$)alkyl; or —(C$_1$-C$_6$)alkoxy; or R$^a$ and R$^b$, taken together with the nitrogen atom to which they are attached, form a 5- or 6-membered heterocycloalkyl ring, optionally having from one to three additional heteroatoms independently selected from the group consisting of nitrogen, oxygen, and sulfur, wherein said 5- or 6-membered heterocycloalkyl ring is optionally, and independently, substituted with from one to three halogen; —(C$_1$-C$_6$)alkyl; or heteroaryl, optionally substituted independently with from one to three halogen; trifluoromethyl; and cyano; and R$^1$ and R$^2$ are, independently, (ii) hydrogen; (iii) halogen; (iv) aryl, optionally substituted independently with from one to three halogen; cyano; —(C$_1$-C$_6$)alkyl; —(C$_1$-C$_6$)alkoxy; —COR$^5$; or —CONR$^3$R$^4$; (v) —(C$_1$-C$_6$)alkyl, optionally substituted independently with from one to three aryl, optionally substituted independently with from one to three halogen or trifluoromethyl; heteroaryl; —CONR$^3$R$^4$; or hydroxy; (vi) —COR$^5$; (vii) —CONR$^3$R$^4$; or (viii) —(C$_1$-C$_6$)cycloalkyl, optionally substituted independently with from one to three —COR$^5$.

A generally preferred subgroup of the compounds of formula (I) comprises those compounds wherein:

R$^a$ and R$^b$ are, independently:

(1) hydrogen;

(3) —(C$_1$-C$_6$)alkyl, optionally, and independently, substituted with from one to three:

(A) cyano; (B) halogen; (C) —NR$^3$R$^4$; (D) —COR$^5$; (E) —OR$^6$; (F) —SR$^6$; (G) —S(O)R$^6$; (H) —SO$_2$R$^6$; (I) aryl, optionally substituted independently with from one to three halogen; nitro; —SO$_2$NH$_2$; —(C$_1$-C$_6$)alkyl; methylenedioxy; —COR$^5$; or —OR$^6$; (J) heteroaryl, optionally substituted independently with from one to three hydroxy; nitro; halogen; —OR$^6$; aryl, optionally substituted independently with —(C$_1$-C$_6$)alkyl; heteroaryl; trifluoromethyl; or —(C$_1$-C$_6$)alkoxy, optionally substituted with hydroxy; (K) —(C$_3$-C$_{11}$)cycloalkyl, optionally substituted independently from one to three cyano; —COR$^5$; or —CH$_2$NR$^3$R$^4$; or (L) —(C$_3$-C$_{11}$)heterocycloalkyl, optionally substituted independently with from one to three —(C$_1$-C$_6$)alkyl, optionally substituted with aryl; —COR$^5$; aryl, optionally substituted independently with halogen; oxo; or —(C$_1$-C$_6$)alkoxy; wherein:

R$^3$ and R$^4$ are independently:

(a) hydrogen; (b) —SO$_2$R$^6$; (c) aryl, optionally substituted independently with from one to three halogen; cyano; nitro; —(C$_1$-C$_6$)alkyl, —(C$_1$-C$_6$)alkoxy, or —COR$^5$; (d) —(C$_1$-C$_6$) alkyl, optionally substituted independently with from one to three —(C$_3$-C$_{11}$)heterocycloalkyl; —(C$_3$-C$_{11}$)cycloalkyl; —(C$_1$-C$_6$)alkoxy; aryl; or heteroaryl; (e) heteroaryl, optionally substituted independently with from one to three halogen; trifluoromethyl; cyano; nitro; —COR$^5$; —(C$_1$-C$_6$)alkyl, optionally substituted with —(C$_3$-C$_{11}$)heterocycloalkyl; or —(C$_1$-C$_6$)alkoxy; (f) —(C$_3$-C$_{11}$)heterocycloalkyl, optionally substituted independently with from one to three —(C$_1$-C$_6$) alkyl; or (g) —COR$^5$; or R$^3$ and R$^4$, taken together with the nitrogen atom to which they are attached, form a 5- or 6-membered heterocycloalkyl ring, optionally having from one to three additional heteroatoms independently selected from nitrogen, oxygen, and sulfur, wherein said 5- or 6-membered heterocycloalkyl ring is optionally substituted with from one to three —(C$_1$-C$_6$)alkyl, optionally substituted with aryl;

R$^5$ is (h) hydroxy; (i) —(C$_1$-C$_6$)alkyl, optionally substituted independently with from one to three —CO$_2$H; —(C$_1$-C$_6$)alkoxy; or aryl; (j) —(C$_1$-C)alkoxy; (k) aryl, optionally substituted with halogen; (l) heteroaryl; or (m) —(C$_3$-C$_{11}$) heterocycloalkyl, optionally substituted independently with from one to three oxo; —CO$_2$H; or —(C$_1$-C$_6$)alkyl; and R$^6$ is (n) hydrogen; (o) —(C$_1$-C$_6$)alkyl, optionally substituted independently with from one to three hydroxy; —(C$_1$-C$_6$)alkoxy; aryl, optionally substituted with halogen; or heteroaryl, optionally substituted with —CH$_2$NR$^3$R$^4$; (p) aryl, optionally substituted independently with from one to three halogen; —(C$_1$-C$_6$)alkyl; cyano; trifluoromethyl; or —OR$^6$; (q) heteroaryl, optionally substituted independently with from one to three amino; —(C$_1$-C$_6$)alkyl; —(C$_1$-C$_6$)alkoxy; or —COR$^5$; or (r) —(C$_3$-C$_{11}$)heterocycloalkyl, optionally substituted independently with from one to three —(C$_1$-C$_6$) alkyl;

(4) —(C$_3$-C$_{11}$)cycloalkyl; or (5) —(C$_3$-C$_{11}$)heterocycloalkyl, optionally substituted independently with from one to three halogen; —COR$^5$; —(C$_1$-C$_6$)alkyl; or —(C$_1$-C$_6$)alkoxy; and R$^1$ and R$^2$ are, independently, (ii) hydrogen; (iv) aryl, optionally substituted independently with from one to three halogen; cyano; —(C$_1$-C$_6$)alkyl; —(C$_1$-C$_6$)alkoxy; —COR$^5$; or —CONR$^3$R$^4$; or (v) —(C$_1$-C$_6$)alkyl, optionally substituted independently with from one to three aryl, optionally substituted independently with from one to three halogen or trifluoromethyl; heteroaryl; —CONR$^3$R$^4$; or hydroxy.

An especially preferred subgroup of the compounds of formula (I) comprises those compounds wherein:

R$^a$ and R$^b$ are, independently:

(1) hydrogen;

(3) —(C$_1$-C$_6$)alkyl, optionally, and independently, substituted with one or two:

(A) cyano; (E) —OR$^6$; (F) —SR$^6$; (I) aryl, optionally substituted with nitro; (J) heteroaryl, optionally substituted independently with one or two —OR$^6$ or —(C$_1$-C$_6$)alkyl; or (L) —(C$_3$-C$_{11}$)heterocycloalkyl, optionally substituted with oxo or —COR$^5$; wherein R$^6$ is (n) hydrogen; (o) —(C$_1$-C$_6$)alkyl; (p) aryl, optionally substituted with cyano or —OR$^6$; or (q) heteroaryl, optionally substituted with amino; —(C$_1$-C$_6$) alkyl; —(C$_1$-C$_6$)alkoxy; or —COR$^5$;

(4) —$(C_3-C_{11})$cycloalkyl; or (5) —$(C_3-C_{11})$heterocycloalkyl, optionally substituted with —$COR^5$; wherein $R^5$ is (h) hydroxy; (i) —$(C_1-C_6)$alkyl; or (j) —$(C_1-C_6)$alkoxy; and $R^1$ and $R^2$ are, independently, hydrogen or —$(C_1-C_6)$alkyl.

The compounds and intermediates of the present invention may be named according to either the IUPAC (International Union for Pure and Applied Chemistry) or CAS (Chemical Abstracts Service, Columbus, Ohio) nomenclature systems.

The carbon atom content of the various hydrocarbon-containing moieties may be indicated by a prefix designating the minimum and maximum number of carbon atoms in the moiety, i.e., the prefix "—$(C_a-C_b)$alkyl" indicates an alkyl moiety of the integer "a" to "b" carbon atoms, inclusive.

The term "alkoxy" denotes straight or branched, monovalent, saturated aliphatic chains of carbon atoms bonded to an oxygen atom, wherein the alkoxy group optionally incorporates one or more double or triple bonds, or a combination of double bonds and triple bonds. Examples of alkoxy groups include methoxy, ethoxy, propoxy, butoxy, isobutoxy, tert-butoxy, and the like.

The term "alkyl" denotes straight, or branched, monovalent chains of carbon atoms, wherein the alkyl group optionally incorporates one or more double or triple bonds, or a combination of double bonds and triple bonds. Examples of alkyl groups include methyl, ethyl, propyl, isopropyl, butyl, isobutyl, vinyl, allyl, 2-methylpropenyl, 2-butenyl, 1,3-butadienyl, ethynyl, propargyl, and the like.

The term "aryl" denotes a monocyclic, or polycyclic, aromatic hydrocarbon. Examples of aryl groups include anthracenyl, fluorenyl, phenanthrenyl, phenyl, naphthyl, and the like.

The term "cycloalkyl" denotes a saturated monocyclic, or polycyclic, cycloalkyl group, optionally fused to an aryl group, wherein the cycloalkyl group optionally incorporates one or more double or triple bonds, or a combination of double bonds and triple bonds, but which is not aromatic. Examples of cycloalkyl groups include adamantanyl, cyclopropyl, cyclobutyl, cyclopentyl, cyclohexyl, cycloheptyl, decahydronaphthalinyl, norbornanyl, and the like.

The term "halogen" represents chloro, fluoro, bromo, and iodo.

The term "heteroaryl" denotes a monocyclic, or polycyclic, aromatic hydrocarbon group wherein one or more carbon atoms have been replaced with heteroatoms selected from the group consisting of nitrogen, oxygen, and sulfur. If the heteroaryl group contains more than one heteroatom, the heteroatoms may be the same or different. Examples of heteroaryl groups include acridinyl, benzofuranyl, benzothienyl, benzimidazolyl, benzoxazolyl, benzothiazolyl, chromenyl, cinnolinyl, furyl, imidazolyl, indazolyl, indolizinyl, indolyl, isobenzofuranyl, isoindolyl, isoquinolyl, isothiazolyl, isoxazolyl, naphthyridinyl, oxadiazolyl, oxazinyl, oxazolyl, phenazinyl, phthalazinyl, pteridinyl, purinyl, pyranyl, pyrazinyl, pyrazolyl, pyridazinyl, pyrido[3,4-b]indolyl, pyridyl, pyrimidyl, pyrrolyl, quinolizinyl, quinolyl, quinoxalinyl, thiadiazolyl, thiatriazolyl, thiazolyl, thienyl, triazinyl, triazolyl, xanthenyl, and the like.

The term "heterocycloalkyl" denotes a saturated, or partially unsaturated, monocyclic, or polycyclic, cycloalkyl group, optionally fused to an aromatic or heteroaromatic hydrocarbon group, in which at least one of the carbon atoms has been replaced with a heteroatom selected from the group consisting of nitrogen, oxygen, and sulfur. If the heterocycloalkyl group contains more than one heteroatom, the heteroatoms may be the same or different. Examples of such heterocycloalkyl groups include azabicycloheptanyl, azetidinyl, benzazepinyl, 1,3-dihydroisoindolyl, dioxolanyl, dioxanyl, carbazolyl, dioxolanyl, dithianyl, indolinyl, imidazolidinyl, morpholinyl, quinuclidinyl, phenothiazinyl, phenoxazinyl, piperazinyl, piperidyl, pyrazolidinyl, pyrrolidinyl, tetrahydrofuryl, tetrahydroindolyl, tetrahydroisoquinolinyl, tetrahydropyranyl, tetrahydroquinolinyl, tetrahydroquinoxalinyl, tetrahydrothiopyranyl, tetrahydro-2H-1,4-thiazinyl, thiazolidinyl, thiomorpholinyl, thioxanthenyl, thioxanyl, trithianyl, and the like.

A cyclic group may be bonded to another group in more than one way. If no particular bonding arrangement is specified, then all possible arrangements are intended. For example, the term "pyridyl" includes 2-, 3-, or 4-pyridyl, and the term "thienyl" includes 2- or 3-thienyl.

The term "mammal" means animals including, for example, dogs, cats, cows, sheep, horses, and humans. Preferred mammals include humans of either gender.

The term "oxo", when used within the context of "heterocycloalkyl", indicates a carbonyl group substituent formed between a ring carbon atom(s) of the heterocycloalkyl group and an oxygen atom.

The phrase "pharmaceutically acceptable" indicates that the designated carrier, vehicle, diluent, excipient(s), and/or salt must be chemically and/or physically compatible with the other ingredients comprising the formulation, and physiologically compatible with the recipient thereof.

The term "prodrug" refers to a compound that is a drug precursor which, following administration, releases the drug in vivo via a chemical or physiological process (e.g., upon being brought to physiological pH or through enzyme activity). A discussion of the preparation and use of prodrugs is provided by T. Higuchi and W. Stella, "Prodrugs as Novel Delivery Systems, Vol. 14 of the ACS Symposium Series, and in Bioreversible Carriers in Drug Design, ed. Edward B. Roche, American Pharmaceutical Association and Pergamon Press, 1987.

The term "radical" denotes a group of atoms that behaves as a single reactant in a chemical reaction, e.g., an organic radical is a group of atoms that imparts characteristic properties to a compound containing it, or which remains unchanged during a series of reactions, or transformations.

The term "salts" refers to organic and inorganic salts of a compound of formula (I), or a prodrug thereof. These salts can be prepared in situ during the final isolation and purification of a compound, or by separately reacting a compound of formula (I), or a prodrug thereof, with a suitable organic or inorganic acid or base and isolating the salt thus formed. Representative salts include the hydrobromide, hydrochloride, sulfate, bisulfate, nitrate, acetate, oxalate, besylate, palmitate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. These may also include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. For additional examples see, for example, Berge, et al., J. Pharm. Sci., 66, 1-19 (1977).

The term "substituted" means that a hydrogen atom on a molecule has been replaced with a different atom or molecule. The atom or molecule replacing the hydrogen atom is denoted as a "substituent."

The symbol "-" represents a covalent bond.

The phrase "reaction-inert solvent" or "inert solvent" refers to a solvent, or mixture of solvents, that does not interact with starting materials, reagents, intermediates, or products in a manner that adversely affects their desired properties.

The terms "treating", "treated", or "treatment" as employed herein includes preventative (e.g., prophylactic), palliative, or curative use or result.

The compounds of formula (I) may contain asymmetric or chiral centers and, therefore, exist in different stereoisomeric forms. It is intended that all stereoisomeric forms of the compounds and prodrugs of formula (I) as well as mixtures thereof, including racemic mixtures, form part of the present invention. In addition, the present invention embraces all geometric and positional isomers. For example, if a compound or prodrug of formula (I) incorporates a double bond, both the cis- and trans-forms, as well as mixtures thereof, are embraced within the scope of the invention.

Diastereomeric mixtures can be separated into their individual diastereomers on the basis of their physical chemical differences by methods well-known to those of ordinary skill in the art, such as by chromatography and/or fractional crystallization. Enantiomers can be separated by converting the enantiomeric mixture into a diasteriomeric mixture by reaction with an appropriate optically active compound (e.g., alcohol), separating the diasteriomers and converting (e.g., hydrolyzing) the individual diasteriomers to the corresponding pure enantiomers. Also, some of the compounds of formula (I) may be atropisomers (e.g., substituted biaryls) and are also considered as part of the invention.

The compounds and prodrugs of formula (I) may exist in unsolvated as well as solvated forms with pharmaceutically acceptable solvents, such as water, ethanol, and the like, and it is intended that the invention embrace both solvated and unsolvated forms.

It is also possible that the compounds and prodrugs of formula (I) may exist as tautomeric isomers in equilibrium, and all such forms are embraced within the scope of the invention.

The present invention also embraces isotopically-labeled compounds of formula (I), which are identical to those recited herein, but for the fact that one or more atoms are replaced by an atom having an atomic mass or mass number different from the atomic mass or mass number usually found in nature. Examples of isotopes that can be incorporated into compounds of formula (I) include isotopes of hydrogen, carbon, nitrogen, oxygen, phosphorus, fluorine, and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. The compounds of formula (I), the prodrugs thereof, and the pharmaceutically acceptable salts of the compounds and prodrugs, that contain the aforementioned isotopes and/or other isotopes of the other atoms are intended to be within the scope of the instant invention.

Certain isotopically-labeled compounds of formula (I), for example those compounds into which radioactive isotopes such as $^3H$ and $^{14}C$ are incorporated, are useful in compound and/or substrate tissue distribution assays. Tritiated, i.e., $^3H$, and carbon-14, i.e., $^{14}C$, isotopes are particularly preferred for their relative ease of preparation and facile detection. Furthermore, substitution with heavier isotopes such as deuterium, i.e., $^2H$, may afford certain therapeutic advantages resulting from greater metabolic stability, for example, increased in vivo half-life, or reduced dosage requirements and, hence, may be preferred in some circumstances. The isotopically-labeled compounds of formula (I) can generally be prepared by carrying out procedures analogous to those disclosed in the Schemes and/or Examples set forth hereinbelow, by substituting an isotopically-labeled reagent for a non-isotopically-labeled reagent.

In another aspect, the invention provides methods of treating glycogen synthase kinase-3-mediated conditions, diseases, or symptoms in a mammal in need of such treatment which comprise administering to a mammal in need of such treatment a therapeutically effective amount of a compound of formula (I), a prodrug thereof, or a pharmaceutically acceptable salt of the compound or prodrug; a pharmaceutical composition comprising a compound of formula (I), a prodrug thereof, or a pharmaceutically acceptable salt of the compound or prodrug, and a pharmaceutically acceptable carrier, vehicle, or diluent; or a combination of an amount of a compound of formula (I), a prodrug thereof, or a pharmaceutically acceptable salt of the compound or prodrug, and an amount of one or more of: (i) an anti-angiogenesis agent, (ii) a signal transduction inhibitor, (iii) an anti-proliferative agent, (iv) an NK-1 receptor antagonist, (v) a $5HT_{1D}$ receptor antagonist, (vi) a selective serotonin reuptake inhibitor (SSRI), (vii) an anti-psychotic agent, (viii) an acetylcholinesterase inhibitor, (ix) a neuroprotectant, (x) tissue plasminogen activator (TPA), (xi) neutrophil inhibitory factor (NIF), and (xii) a potassium channel modulator; or a pharmaceutical composition comprising the aforementioned combinations.

Preferred conditions, diseases, and symptoms treatable according to the instant methods are those selected from the group consisting of Alzheimer's Disease, asthma, atherosclerosis, anxiety, bipolar disorder, cancer, diabetes, dementia, depression, frailty, hair loss, heart failure, essential hypertension, hyperglycemia, hyperlipidemia, hypoglycemia, inflammation, ischemia, male fertility and sperm motility, mood disorders, neuronal cell death, obesity, obsessive compulsive disorder, polycystic ovary disorder, schizophrenia, stroke, Syndrome X, and traumatic brain injury. An especially preferred disease treatable according to the instant methods is diabetes.

Frailty is characterized by the progressive loss of skeletal muscle mass resulting in a high risk of injury from fall, difficulty in recovery from illness, prolongation of hospitalization, and long-term disability requiring assistance in daily living. The reduction of muscle mass and physical strength typically leads to diminished quality of life, loss of independence, and mortality. Frailty is normally associated with aging, but may also result when muscle loss and reduced strength occur due to other factors, such as disease-induced cachexia, immobilization, or drug-induced sarcopenia. Another term that has been used to denote frailty is sarcopenia, which is a generic term for the loss of skeletal muscle mass, or quality. Examples of skeletal muscle properties that contribute to its overall quality include contractility, fiber size and type, fatiguability, hormone responsiveness, glucose uptake/metabolism, and capillary density.

Generally preferred anti-angiogenesis agents may comprise, for example, matrix metalloproteinase-2 (MMP-2) inhibitors, matrix metalloproteinase-9 (MMP-9) inhibitors, and cyclooxygenase-II (COX-II) inhibitors. Examples of useful MMP-2 and MMP-9 inhibitors are disclosed in, for example, PCT International Application Publication Nos. WO 98/34915 and WO 98/34918, and U.S. Pat. Nos. 5,240,958; 5,310,763; 5,455,258; 5,506,242; 5,530,161; 5,552,419; 5,672,615; 5,861,510; 5,863,949; 5,932,595; 5,994,351; 6,077,864; 6,087,392; 6,090,852; 6,110,964; 6,147,061; 6,147,074; 6,303,636; 6,380,219; and 6,387,931. Examples of COX-II inhibitors useful in the present combinations and methods comprise CELEBREX® (celecoxib, U.S. Pat. No. 5,466,823), valdecoxib (U.S. Pat. No. 5,633,272), and rofecoxib (U.S. Pat. No. 5,474,995). Generally preferred MMP-2 and MMP-9 inhibitors are those exhibiting little or no activity inhibiting MMP-1. Especially preferred MMP-2 and MMP-9 inhibitors are those that selectively inhibit MMP-2 and/or MMP-9 relative to other MMP inhibitors, i.e., MMP-1, MMP-3, MMP-4, MMP-5, MMP-6, MMP-7, MMP-8, MMP-10, MMP-11, MMP-12, and MMP-13. Specific examples of MMP inhibitors useful in the present combinations and methods comprise AG-3340, RO 32-3555, RS 13-0830, and the following compounds:

3-[[4-(4-fluoro-phenoxy)-benzenesulfonyl]-(1-hydroxy-carbamoyl-cyclopentyl)-amino]-propionic acid;

3-exo-3-[4-(4-fluoro-phenoxy)-benzenesulfonyl-amino]-8-oxa-bicyclo[3.2.1]octane-3-carboxylic acid hydroxyamide;

(2R,3R)1-[4-(2-chloro-4-fluorobenzyloxy)-benzenesulfonyl]-3-hydroxy-3-methyl-piperidine-2-carboxylic acid hydroxyamide;

4-[4-(4-fluoro-phenoxy)-benzenesufonyl-amino]-tetrahydro-pyran-4-carboxlyic acid hydroxyamide;

3-[[4-(4-fluoro-phenoxy)-benzenesulfonyl]-(1-hydroxy-carbamoyl-cyclobutyl)-amino]-propionic acid;

4-[4-(4-chloro-phenoxy)-benzenesulfonyl-amino]-tetrahydro-pyran-4-carboxlyic acid hydroxyamide;

(R)-3-[4-(4-chloro-phenoxy)-benzenesulfonyl-amino]-tetrahydro-pyran-3-carboxlyic acid hydroxyamide;

(2R,3R)1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxy-carbamoyl-1-methyl-ethyl)-amino]-propionic acid;

3-[[4-(4-fluoro-phenoxy)-benzenesulfonyl]-(4-hydroxy-carbamoyl-tetrahydro-pyran-4-yl)-amino]-propionic acid;

3-exo-3-[4-(4-chloro-phenoxy)-benzenesulfonyl-amino]-8-oxa-bicyclo[3.2.1]octane-3-carboxylic acid hydroxyamide;

3-endo-3-[4-(4-fluoro-phenoxy)-benzenesulfonyl-amino]-8-oxa-bicyclo[3.2.1]octane-3-carboxylic acid hydroxyamide; and (R)-3-[4-(4-fluoro-phenoxy)-benzenesulfonyl-amino]-tetrahydro-furan-3-carboxlyic acid hydroxyamide; and the pharmaceutically acceptable salts and solvates thereof.

Generally preferred signal transduction inhibitors may comprise, for example, epidermal growth factor receptor (EGFR) response inhibitors, such as EGFR antibodies, EGF antibodies, and molecules that are EGFR inhibitors; vascular endothelial growth factor (VEGF) inhibitors; and erbB2 receptor inhibitors, such as molecules or antibodies that bind to the erbB2 receptor, for example, HERCEPTIN® (Genentech Inc.; South San Francisco, Calif.). EGFR inhibitors are described in, for example, PCT International Application Publication No. WO 98/14451, and U.S. Pat. Nos. 5,679,683; 5,747,498; and 6,391,874. EGFR-inhibiting agents may comprise, for example, the monoclonal antibodies C225 and ant-EGFR 22Mab (Imclone Systems, Inc.), ZD-1839, BIBX-1382, MDX-103, VRCTC-310, and EGF fusion toxin (Seragen Inc.; Hopkinton, Mass.). VEGF inhibitors are disclosed in, for example, PCT International Application Publication No. WO 99/24440, and U.S. Pat. Nos. 5,792,783; 5,834,504; 5,851,999; 5,883,113; 5,886,020; 6,051,593; 6,114,371; 6,133,305; 6,162,804; 6,174,889; 6,207,669; 6,235,741; 6,291,455; 6,294,532; 6,310,238; 6,380,203; and 6,395,734. Specific VEGF inhibitors may comprise, for example, Su-5416, IM862, anti-VEGF monoclonal antibody (Cytran Inc.; Kirkland, Wash.), and angiozyme (Ribozyme; Boulder, Colo.). ErbB2 receptor inhibitors are disclosed in, for example, PCT International Application Publication Nos. WO 97/13760, WO 99/35132, and WO 99/35146, and U.S. Pat. Nos. 5,679,683; 5,587,458; 5,877,305; 6,207,669; and 6,391,874. Specific erbB2 receptor inhibitors may comprise, for example, GW-282974 (Glaxo Wellcome pic.), and the monoclonal antibody AR-209 (Aronex Pharmaceuticals Inc.; The Woodlands, Tex.).

Generally preferred anti-proliferative agents may comprise, for example, cytotoxic lymphocyte antigen 4 (CTLA4) antibodies, and other agents capable of blocking CTLA4; and farnesyl transferase inhibitors.

Examples of NK-1 receptor antagonists are disclosed in, for example, U.S. Pat. Nos. 5,122,525; 5,162,339; 5,232,929; 5,332,817; 5,703,240; 5,716,965; 5,719,147; 5,744,480; 5,763,699; 5,773,450; 5,807,867; 5,843,966; 5,852,038; 5,886,009; and 5,939,433.

Examples of $5HT_{1D}$ receptor antagonists useful in the present combinations and methods are disclosed in, for example, PCT International Application Publication No. WO 94/21619, and U.S. Pat. Nos. 5,358,948; 5,510,350; 6,380,186; 6,403,592; 6,423,708; and 6,462,048.

Examples of SSRI's useful in the present combinations and methods may comprise, for example, fluoxetine (U.S. Pat. No. 4,314,081), paroxetine (U.S. Pat. No. 4,007,196), sertraline (U.S. Pat. No. 4,536,518), fluvoxamine (U.S. Pat. No. 4,085,225), venlafaxine hydrochloride (EFFEXOR®, U.S. Pat. No. 4,535,186), nefazodone hydrochloride (SERZONE®, U.S. Pat. No. 4,338,317), and bupropion hydrochloride (WELLBUTRIN®, U.S. Pat. Nos. 3,819,706 and 3,885,046).

Generally preferred anti-psychotic agents useful in the present combinations and methods may comprise, for example, ziprasidone (GEODON®, U.S. Pat. No. 5,312,925), olanzapine (U.S. Pat. No. 5,229,382), risperidone (U.S. Pat. No. 4,804,663), L-745,870, sonepiprazole, RP-62203 (fananserin), NGD-941, balaperidone, flesinoxan (U.S. Pat. No. 4,833,142), and gepirone (U.S. Pat. No. 4,423,049).

Generally preferred acetylcholinesterase inhibitors useful in the present combinations and methods may comprise, for example, donepezil (ARICEPT®, U.S. Pat. No. 4,895,841), rivastigmine (EXELON®, U.S. Pat. No. 4,948,807), metrifonate (U.S. Pat. No. 2,701,225), galanthamine, physostigmine, tacrine, huperzine, and icopezil (U.S. Pat. No. 5,538,984).

Generally preferred neuroprotectants useful in the instant combinations and methods may comprise, for example, NMDA receptor antagonists. Specific NMDA receptor antagonists comprise, for example, (1S,2S)-1-(4-hydroxyphenyl)-2-(4-hydroxy-4-phenylpiperidin-1-yl)-1-propanol (U.S. Pat. No. 5,272,160); eliprodil (U.S. Pat. No. 4,690,931); and gavestenel (U.S. Pat. No. 5,373,018). Examples of additional NMDA antagonists are disclosed in, for example, U.S. Pat. Nos. 4,690,931; 5,185,343; 5,272,160;, 5,356,905; 5,373,018; 5,744,483; 5,962,472; 6,046,213; 6,124,317; 6,124,323; 6,130,234; 6,218,404; 6,333,036; and 6,448,270; and in PCT International Application Publication Nos. WO 97/23202 and WO 98/18793.

A generally preferred potassium channel modulator comprises, for example, BMS-204352 (flindokaliner, U.S. Pat. No. 5,602,169).

The disclosures of all of the above U.S. patents are incorporated herein in their entirety by reference.

In another aspect, the invention provides methods for inhibiting glycogen synthase kinase-3 activity in a mammal in need of such inhibition which comprise administering a glycogen synthase kinase-3 inhibiting amount of a compound of formula (I), a prodrug thereof, or a pharmaceutically acceptable salt of the compound or prodrug; or a pharmaceutical composition comprising a compound of formula (I), a prodrug thereof, or a pharmaceutically acceptable salt of the compound or prodrug, and a pharmaceutically acceptable carrier, vehicle, or diluent.

The compounds of formula (I), the prodrugs thereof, and the pharmaceutically acceptable salts of the compounds and prodrugs, may be administered to a mammal at dosage levels in the range of from about 0.0001 mg to about 1,000 mg per day. For a normal adult human having a body mass of about 70 kg, a dosage in the range of from about 0.01 mg to about 500 mg per kg body mass is typically sufficient. However, some variability in the general dosage range may be required depending upon the age and mass of the subject being treated, the intended route of administration, the particular compound being administered, and the like. The determination of dosage ranges and optimal dosages for a particular mammalian subject is within the ability of one of ordinary skill in the art having benefit of the instant disclosure.

According to the methods of the present invention, the compounds of formula (I), the prodrugs thereof, and the pharmaceutically acceptable salts of the compounds and prodrugs, or the aforementioned combinations thereof with the amounts of one or more of: (i) an anti-angiogenesis agent, (ii) a signal transduction inhibitor, (iii) an anti-proliferative agent, (iv) an NK-1 receptor antagonist, (v) a $5HT_{1D}$ receptor antagonist, (vi) a selective serotonin reuptake inhibitor (SSRI), (vii) an anti-psychotic agent, (viii) an acetylcholinesterase inhibitor, (ix) a neuroprotectant, (x) tissue plasminogen activator (TPA), (xi) neutrophil inhibitory factor (NIF), and (xii) a potassium channel modulator, are preferably administered in the form of a pharmaceutical composition comprising a pharmaceutically acceptable carrier, vehicle, or diluent. Accordingly, a compound of formula (I), a prodrug thereof, or a pharmaceutically acceptable salt of the compound or prodrug, or the aforementioned combinations, may be administered to a subject separately, or together, in any conventional oral, rectal, transdermal, parenteral (e.g., intravenous, intramuscular, or subcutaneous), intracisternal, intravaginal, intraperitoneal, intravesical, local (e.g., powder, ointment, or drop), or buccal, or nasal dosage form.

Pharmaceutical compositions suitable for parenteral injection may comprise pharmaceutically acceptable sterile aqueous or nonaqueous solutions, dispersions, suspensions, or emulsions, and sterile powders for extemporaneous reconstitution into sterile injectable solutions or dispersions. Examples of suitable aqueous and nonaqueous carriers, vehicles, and diluents include water, ethanol, polyols (such as propylene glycol, polyethylene glycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions, and by the use of surfactants.

The pharmaceutical compositions of the invention may further comprise adjuvants, such as preserving, wetting, emulsifying, and dispersing agents. Prevention of microorganism contamination of the instant compositions can be accomplished with various antibacterial and antifungal agents, for example, parabens, chlorobutanol, phenol, sorbic acid, and the like. It may also be desirable to include isotonic agents, for example, sugars, sodium chloride, and the like.

Prolonged absorption of injectable pharmaceutical compositions may be effected by the use of agents capable of delaying absorption, for example, aluminum monostearate and gelatin.

Solid dosage forms for oral administration include capsules, tablets, powders, and granules. In such solid dosage forms, the active compound is admixed with at least one inert conventional pharmaceutical excipient (or carrier) such as sodium citrate or dicalcium phosphate, or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid certain complex silicates, and sodium carbonate; (e) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and/or (i) lubricants, as for example, talc, calcium stearate, magnesium stearate, solid polyethylene glycols, sodium lauryl sulfate, or mixtures thereof. In the case of capsules and tablets, the dosage forms may further comprise buffering agents.

Solid compositions of a similar type may also be employed as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well-known to one of ordinary skill in the art. They may also comprise opacifying agents, and can also be of such composition that they release the active compound(s) in a delayed, sustained, or controlled manner. Examples of embedding compositions that can be employed are polymeric substances and waxes. The active compound(s) can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the pharmaceutical composition can also include adjuvants, such as wetting agents, emulsifying and suspending agents, sweetening, flavoring, and perfuming agents.

Suspensions, in addition to the active compound(s), may further comprise suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of the aforementioned substances, and the like.

Compositions for rectal or vaginal administration preferably comprise suppositories, which can be prepared by mixing an active compound(s) with suitable non-irritating excipients or carriers such as cocoa butter, polyethylene glycol or a suppository wax, which are solid at ordinary room temperature, but liquid at body temperature, and therefore, melt in the rectum or vaginal cavity thereby releasing the active component.

Dosage forms for topical administration may comprise ointments, powders, sprays and inhalants. The active agent(s) are admixed under sterile condition with a pharmaceutically acceptable carrier, vehicle, or diluent, and any preservatives, buffers, or propellants that may be required.

The compounds of formula (I), the prodrugs thereof, and the pharmaceutically acceptable salts of the compounds and prodrugs, may be prepared according to the exemplary synthetic routes disclosed in the Schemes and Examples hereinbelow, as well as by other conventional organic preparative methods known, or apparent in light of the instant disclosure, to one of ordinary skill in the relevant art. It is to be understood that the methods disclosed in the instant Schemes are intended for purposes of exemplifying the instant invention, and are not to be construed in any manner as limitations thereon.

A generalized method for preparing the compounds of formula (I) is depicted in Scheme 1 hereinbelow. Alternative synthetic routes for the preparation of compounds of formula (I) wherein $R^a$, $R^b$, $R^1$, and/or $R^2$ comprise specifically articulated functional groups are set forth hereinbelow in Schemes 4 to 7.

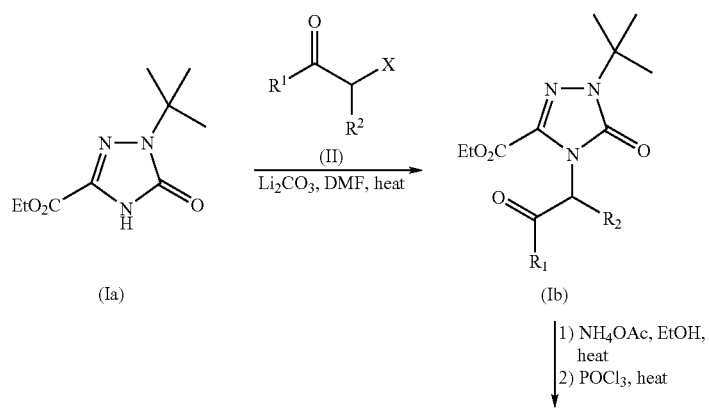

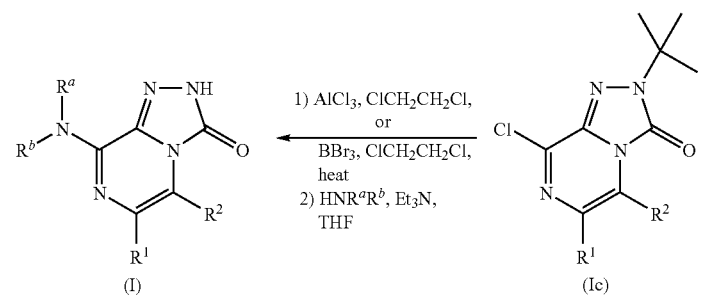

In Scheme 1, a triazolone ester precursor (Ia), preferably protected on N-3 with a tert-butyl group, is alkylated with an α-haloketone derivative (II) (X=Br or Cl) in the presence of a base, preferably lithium carbonate, in a polar solvent, preferably N,N-dimethylformamide (DMF). The triazolone ester (Ia) and the α-haloketone derivative (II) can be prepared as outlined hereinbelow in Schemes II and III, respectively. The alkylated product (Ib) is then cyclized with an amine, preferably ammonium acetate, in a polar protic solvent, preferably ethanol (EtOH), and the intermediate lactam is then converted into iminochloride (Ic) by reaction with an appropriate chlorinating agent, such as phosphorus oxychloride. Iminochloride (Ic) is then deprotected by treatment with a Lewis Acid, preferably aluminum trichloride or boron tribromide, in warm methylene chloride. Reaction of (Ic) with an appropriately-substituted amine in a solvent such as tetrahydrofuran (THF) in the presence of an organic base, such as triethylamine, affords compound (I). Alternatively, (Ic) may be first treated with the appropriately-substituted amine, followed by deprotection with boron tribromide in warm methylene chloride, to afford (I).

The protected triazolone ester (Ia) may be prepared as disclosed in Scheme 2, Routes A or B hereinbelow.

Alternatively, as disclosed in Route B, ethyl cyanoformate may be converted into the imidate by treatment with an appropriate alcohol, preferably EtOH, and saturating with anhydrous acid, preferably hydrochloric acid. Reaction of the imidate with tert-butyl hydrazine in the presence of an organic base, preferably triethylamine, in a polar protic solvent, preferably EtOH, provides the corresponding hydrazinoiminoacetic acid derivative. Reaction of this intermediate with an appropriate electrophilic carbon monoxide equivalent, preferably 1,1'-carbonyldiimidazole (CDI), in a suitable solvent, such as THF, provides (Ia). Triazolone ester (Ia) may also be prepared by treating ethyl cyanoformate with tert-butyl hydrazine in the presence of N-acetylcystine in a buffered protic solvent, preferably a sodium acetate buffer in EtOH. Reaction of the intermediate so formed with an appropriate electrophilic carbon monoxide equivalent, preferably CDI or triphosgene, in a suitable solvent, preferably THF, affords (Ia).

The α-haloketones (II) required for alkyating triazolone ester (Ia) according to the method in Scheme 1 may be prepared as disclosed in Scheme 3, Routes A or B hereinbelow.

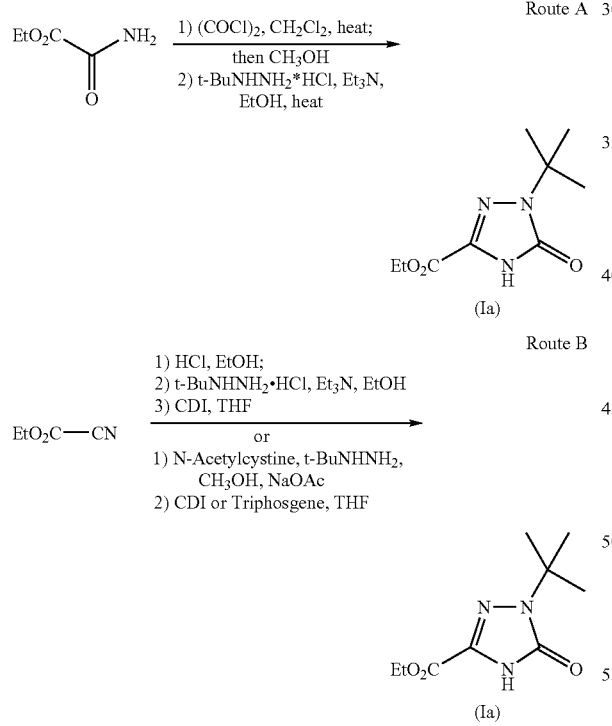

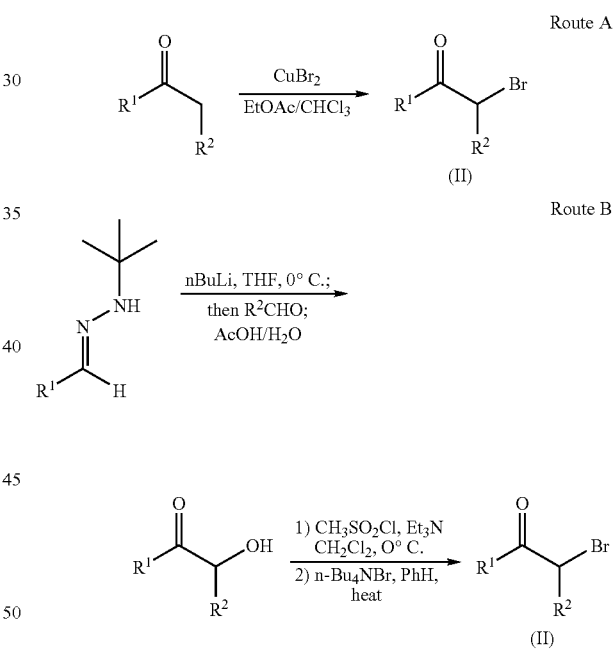

In Scheme 2, Route A, the protected triazolone ester (Ia) may be synthesized from ethyl oxamate through initial isocyanate formation by treatment with an appropriate acylating agent, preferably oxalyl chloride, followed by treatment with an alcohol, preferably methanol (MeOH). Warming the resulting oxoacetic acid derivative with tert-butyl hydrazine in the presence of an organic base, preferably triethylamine, in a polar protic solvent, preferably EtOH, provides (Ia).

In Scheme 3, Route A, an appropriately-substituted ketone is preferably reacted with cuprous bromide in an organic solvent mixture, preferably chloroform and ethyl acetate (J. Org. Chem., 29, 3459 (1964)), to provide (II).

Alternatively, in Scheme 3, Route B, α-bromoketone (II) may be prepared from the corresponding α-hydroxyketone following conversion thereof into an acceptable leaving group using a sulfonyl chloride, preferably methanesulfonyl chloride, preferably followed by displacement with tetrabutylammonium bromide. The α-hydroxy ketone starting materials may be readily prepared using hydrazone alkylation technology (Tetrahedron, 42, 4223 (1986)).

The compounds of formula (I) where $R^1$ and $R^2$ are regioisomeric phenyl groups may be prepared according to the methods disclosed hereinbelow in Schemes 4 and 5.

Scheme 4

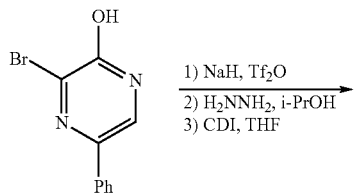

In Scheme 4, 2-hydroxy-3-bromo-5-phenylpyrazine (J. Het. Chem., 665 (1978)) is functionalized as the trifluoromethanesulfonate (triflate) derivative using strong base, preferably sodium hydride, and trifluoromethane sulfonic anhydride. Subsequent displacement of the triflate leaving group with hydrazine is effected in a polar solvent, preferably isopropanol (IPA), and the resulting hydrazine adduct is cyclized using an appropriate electrophilic carbon monoxide equivalent, preferably CDI, in a suitable solvent, such as THF, to afford (III). Treatment of (III) with an appropriately-substituted amine, preferably in a solvent such as THF provides (I).

Scheme 5

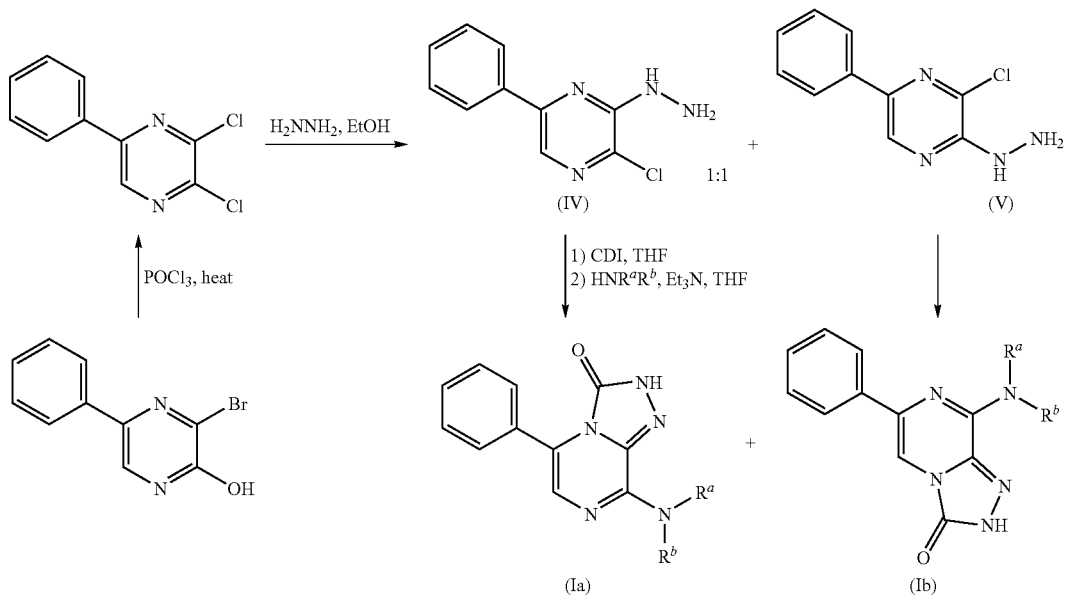

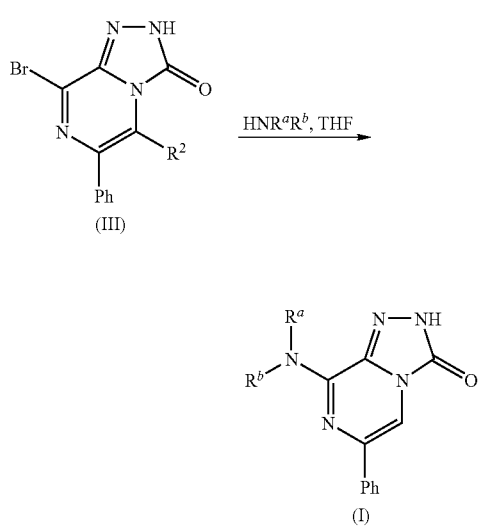

In Scheme 5, regioisomeric 5- and 6-phenyl-substituted analogs of (I) may be prepared by first converting 2-hydroxy-3-bromo-5-phenylpyrazine into 2,3-dichloro-5-phenylpyrazine by treatment with an appropriate electrophilic reagent, preferably phosphorus oxychloride. Reaction of the resulting di-chloro derivative with hydrazine affords hydrazine adducts (IV) and (V) which are both then cyclized to the corresponding triazolone iminochloride by treatment with an appropriate carbon monoxide equivalent, preferably CDI, in a suitable solvent, such as THF. Treatment of the iminochloride with an appropriately-substituted amine in a suitable solvent, preferably THF, affords the regioisomeric 5- and 6-phenyl[1,2,4]triazolo[4,3-a]-3-ones (Ia) and (Ib) respectively.

The compounds of formula (I) wherein $R^1$ is Br, —COOH, or —C(O)NR'R", wherein R' and R" each represent, independently, hydrogen, optionally substituted ($C_1$-$C_6$)alkyl, ($C_3$-$C_8$)alkyl, and the like, or wherein R' and R", taken together with the nitrogen atom to which they are attached, form an optionally substituted heterocycloalkyl ring system, may be prepared as disclosed in Scheme 6 hereinbelow.

Scheme 6

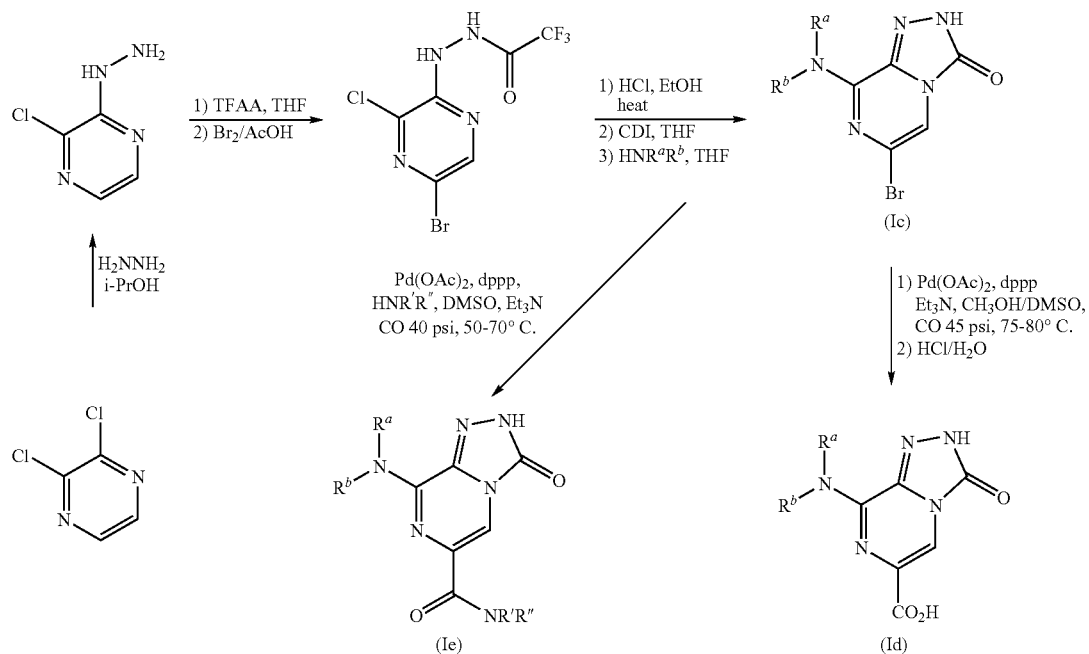

In Scheme 6, the reaction of 2,3-dichloropyrazine with hydrazine in a polar protic solvent, preferably IPA, affords the corresponding hydrazine adduct. Treatment of the adduct with an acylating agent, preferably trifluoroacetic anhydride (TFAA), affords the acyl hydrazide which is halogenated with an appropriate electrophilic halogen source, preferably bromine, in an organic acid, preferably acetic acid (AcOH). Removal of the acyl hydrazide is preferably effected using an acid, such as hydrochloric acid, in a polar protic solvent, such as EtOH. The resulting hydrazine is cyclized into the corresponding triazolone iminochloride with an appropriate electrophilic carbon monoxide equivalent, preferably CDI, in a suitable solvent, such as THF. Treatment of the iminochloride with an appropriately-substituted amine $HNR^aR^b$ in THF affords the substituted 6-bromo[1,2,4]triazolo[4,3-a]pyrazin-3-one (Ic). Conversion of (Ic) into the corresponding 6-carboxylic acid derivative (Id) is preferably effected by warming bromide (Ic) with a palladium source, preferably palladium (II) acetate, a bidentate phosphine ligand, preferably bis-diphenylphosphinopropane, and an organic base, preferably triethylamine, in a polar organic solvent, such as a mixture of MeOH and dimethylsulfoxide (DMSO), under a pressurized atmosphere of carbon dioxide, preferably about 45 psi. Conversion of the resulting intermediate ester into the corresponding acid (Id) is achieved by acid hydrolysis, preferably aqueous hydrochloric acid. The carboxylic amide derivatives (Ie) may be prepared by warming bromide (Ic) with a palladium source, preferably palladium (II) acetate, a bidentate phosphine ligand, preferably bis-diphenylphosphinopropane, an appropriately-substituted amine HNR'R", and an organic base, preferably triethylamine, in a polar organic solvent, such DMSO, under a pressurized atmosphere of carbon dioxide, preferably about 40 psi.

The compounds of formula (I) wherein $R^2$ is —C(OH)(R'''), wherein R''' represents alkyl, phenyl, or substituted phenyl, may be prepared as disclosed in Scheme 7 hereinbelow.

Scheme 7

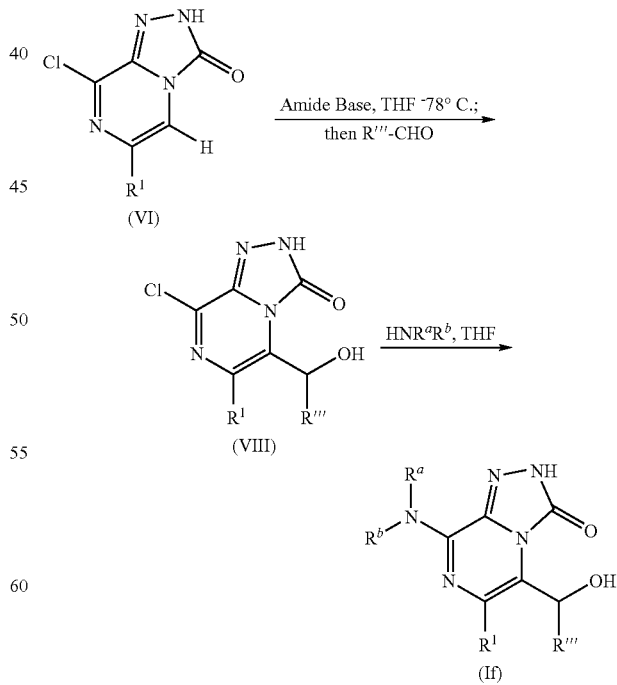

In Scheme 7, the 6-substituted-8-chloro[1,2,4]triazolo[4,3-a]-3-one (VI) is treated with an amide base, preferably lithium 2,2,6,6-tetramethylpiperidide, in a reaction-inert organic solvent, preferably THF, at −78° C. to form a dianion intermediate. Addition of an appropriately-substituted aldehyde R'''—CHO affords iminochloride (VII) which is then treated with an appropriately-substituted amine $HNR^aR^b$, preferably in THF, to provide (If).

Certain compounds of formula (I) incorporate 8-aryloxyamine substrates which substrates may be conveniently prepared according to the methods disclosed hereinbelow in Scheme 8.

Scheme 8

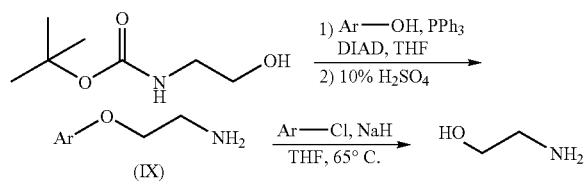

The aryloxyamine starting materials (IX) can be prepared from the coupling of an N-protected ethanolamine derivative, preferably a tert-butylcarbamate, with an appropriately-substituted phenol using an activated diazo compound, preferably diisopropylazodicarboxylate (DIAD), in the presence of a phosphine, preferably triphenylphosphine, in a reaction-inert solvent, such as THF. The coupled product is then deprotected with a protic acid, such as sulfuric acid, to provide (IX). Alternatively, (IX) may be prepared by treating ethanolamine with a strong base, preferably sodium hydride, and reacting the alkoxide so formed with an appropriately-substituted aryl halide. The reaction is typically effected in a reaction-inert solvent, such as THF, at elevated temperature, preferably at, or about, 65° C.

PREPARATIVE EXPERIMENTAL

Unless otherwise noted, all reagents employed were obtained commercially. Unless otherwise noted, the following experimental abbreviations have the meanings indicated:

DMAP—4-(dimethylamino)-pyridine
EtOAc—ethyl acetate
HPLC—high performance liquid chromatography
h—hour(s)
LAH—lithium aluminum hydride
min—minute(s)
mL—milliliter(s)
mmole—millimole(s)
MS—mass spectrometry
NMR—nuclear magnetic resonance
sat.—saturated
TEA—triethylamine
TFA—trifluoroacetic acid The α-bromoketone substrates required for preparing certain compounds of formula (I) were synthesized by brominating α',α'-disubstituted ketones according to the method disclosed in J. Org. Chem., 29, 3459 (1964), or by reacting the lithium anion of isobutyraldehyde tert-butylhydrazone with appropriately-substituted aldehydes (Tetrahedron, 42, 4223 (1986)). Additional α-bromoketones were prepared as outlined hereinbelow in Preparation 1.

Preparation 1

1-Bromo-3-methyl-1-phenyl-butan-2-one

To a solution of 200 mg of 1-hydroxy-3-methyl-1-phenyl-butan-2-one, 169 mg of TEA, and 10 mg of DMAP in methylene chloride (5.6 mL) at 0° C. was added 140 mg of methanesulfonyl chloride. The reaction mixture slowly warmed to ambient temperature over 1.5 h and was then diluted with methylene chloride and washed with 2N HCl solution. The organic layer was dried over sodium sulfate, filtered, and concentrated and the crude mesylate was dissolved in benzene (5.6 mL). This solution was treated with 721 mg of tetra-n-butylammonium bromide and the mixture was warmed to reflux. After one h, the reaction was cooled to ambient temperature and concentrated. The residue was purified by silica gel chromatography to afford the title compound as a light yellow liquid. MS $(M+H^+)=239.1$.

2-Bromo-4-methyl-pentan-3-one (Can. J. Chem., 21, 2212 (1980) and 1-bromo-3-methyl-(3,5-dimethoxy-phenyl)-butan-2-one were prepared according to the procedure disclosed in Preparation 1 using appropriate reactants.

The amine starting materials of formula $R^aR^bNH$ may be prepared according to conventional literature methods, or obtained commercially. General procedures for preparing 2-alkylaminobenzimidazoles are disclosed in Bioorg. Med. Chem., 6, 1185 (1998). Exemplary procedures (Methods A and B) for preparing heterocyclic ethane- and propane-diamines are disclosed hereinbelow in Preparations 2 to 32. Aryloxy amine substrates required for the synthesis of certain compounds of formula (I) were prepared as disclosed hereinbelow in Preparations 33 to 44.

Preparation 2

Method A $N^1$-(7-Trifluoromethyl-quinolin-4-yl)-ethane-1,2-diamine

A mixture of 120 mg of 4-chloro-7-trifluoromethylquinoline and 250 mg of tert-butyl-N-(2-aminoethyl)carbamate was heated to 125° C. for two h. The mixture was cooled to room temperature and partitioned between 10% IPA/chloroform and saturated sodium bicarbonate. The aqueous layer was back extracted with 10% IPA/chloroform and the organic layers were dried over sodium sulfate, filtered and concentrated. The residue was dissolved in EtOAc and washed with water, and the organic layer was dried over sodium sulfate, filtered, and concentrated. The product was dissolved in MeOH (0.5 mL) and stirred with five equiv. of 4.0 M HCl in dioxane for 18 h. The reaction mixture was concentrated and the residue was recrystallized from MeOH to afford the title compound. MS $(M+H)^+=256.1$.

The following 1,2- and 1,3-diamines were prepared in a manner analogous to that described in Preparation 2 using appropriate starting materials.

| Prep'n. | Name | MS (M + H)+ |
|---|---|---|
| 3 | $N^1$-(4-trifluoromethyl-pyrimidin-2-yl)-ethane-1,2-diamine | 205.1 |
| 4 | $N^1$-benzooxazol-2-yl-ethane-1,2-diamine | 176.1 |
| 5 | $N^1$-benzothiazol-2-yl-ethane-1,2-diamine | 194.1 |
| 6 | $N^1$-(5-trifluoromethyl-pyridin-2-yl)-propane-1,3-diamine | 220.1 |
| 7 | $N^1$-(4-trifluoromethyl-pyridin-2-yl)-propane-1,3-diamine | 220.2 |
| 8 | $N^1$-(8-trifluoromethyl-quinolin-4-yl)-ethane-1,2-diamine | 254.1 |
| 9 | $N^1$-(2-trifluoromethyl-quinolin-4-yl)-ethane-1,2-diamine | 254.1 |
| 10 | $N^1$-(6-trifluoromethyl-quinolin-4-yl)-ethane-1,2-diamine | 254.1 |
| 11 | $N^1$-(6-chloro-benzothiazol-2-yl)-ethane-1,2-diamine | 226.0 |
| 12 | $N^1$-(6-methoxy-benzothiazol-2-yl)-ethane-1,2-diamine | 222.1 |
| 13 | 2-(2-amino-ethylamino)-isonicotinic acid | 180.2 |

Preparation 14

Method B $N^1$-Methyl-$N^2$-pyrimidin-2-yl-ethane-1,2-diamine

A solution of 100 mg of N-methylethylenediamine, 245 mg of 2-chloro-5-trifluoromethylpyridine and 261 mg of diisopropylethylamine in toluene was heated at 110° C. for 18 h. The reaction mixture was concentrated, poured into water, and extracted with 10% IPA/chloroform. The organic extracts were dried over sodium sulfate, filtered, and concentrated to provide the desired title compound contaminated with <3% of the bis-substituted dimer. MS (M+H)+=220.2.

The following 1,2-diamines were prepared in a manner analogous to that described in Preparation 14 using appropriate starting materials.

| Prep'n. | Name | MS (M + H)+ |
|---|---|---|
| 15 | $N^1$-(1H-benzoimidazol-2-yl)-ethane-1,2-diamine | 177.2 |
| 16 | $N^1$-(4-trifluoromethyl-pyridin-2-yl)-ethane-1,2-diamine | 206.4 |
| 17 | $N^1$-(pyridin-2-yl)-ethane-1,2-diamine | 138.1 |
| 18 | $N^1$-(quinolin-2-yl)-ethane-1,2-diamine | 206.4 |
| 19 | $N^1$-(pyridin-4-yl)-ethane-1,2-diamine | 137.9 |
| 20 | $N^1$-pyrimidin-2-yl-ethane-1,2-diamine | 139.1 |

Preparation 21

$N^1$-(Pyridin-3-yl)-ethane-1,2-diamine

A mixture of 1.32 g of ethylenediamine, 250 mg of 3-chloropyridine, and 740 mg of potassium tert-butoxide was heated at 118° C. in a sealed tube for 18 h. The reaction was cooled to room temperature, diluted with water and extracted with chloroform. The organic extracts were dried over sodium sulfate, filtered, and concentrated to give the title product as a red oil. MS (M+H)+=137.9.

Preparation 22

$N^1$-Triazin-2-yl-ethane-1,2-diamine

Step A

A solution of 434 mg of tert-butyl-N-(2-aminoethyl)carbamate and 576 mg of sodium carbonate in DMF (9.0 mL) at 0° C. was stirred as a solution of 500 mg of cyanuric chloride in DMF (2.0 mL) was added. The reaction mixture was stirred at 0° C. for two h, at room temperature for three h, and then poured into water to form a white suspension. The solid was collected and the filtrate was extracted with EtOAc and concentrated to provide a crude sample. The solids were combined and purified by silica gel chromatography to give the mono-ethylamine adduct.

Step B

The product from Step A was dissolved in absolute EtOH (7.6 mL) and 50 mg of 10% Pd/C was added, followed by 480 mg of ammonium formate. The mixture was heated at reflux for one h, the solids were removed by filtration through diatomaceous earth, and washed with hot EtOH. The filtrate was concentrated to give a white solid.

Step C

The product of Step B was dissolved in MeOH (1.9 mL) and stirred together with 5 equiv. of 4.0 M HCl in dioxane for two h. The white solid that formed was collected and dried to give the title compound as the hydrochloride salt. MS (M+H)+=140.1.

Preparation 23

$N^1$-(1-Methyl-piperidin-4-yl)-ethane-1,2-diamine

Step A

To a solution of 220 mg of N-methyl-4-piperidone and 283 mg of tert-butyl-(2-amino-ethyl)carbamate in methylene chloride (6.0 mL) was added 563 mg of sodium triacetoxyborohydride and 212 mg of acetic acid. This mixture was stirred at room temperature for 12 days and quenched by the addition of 1N sodium hydroxide, followed by extraction with methylene chloride (4×). The extracts were dried over sodium sulfate, filtered, and concentrated to give a yellow, oily product.

Step B

The product of Step A was dissolved in MeOH (3.0 mL) and stirred with 5 equivalents of 4.0 M HCl in dioxane (3.0 mL) for 18 h. The reaction mixture was concentrated to give the title compound as a light yellow solid. MS (M+H)+= 158.1.

Preparation 24

2-Benzothiazol-2-yl-ethylamine

A solution of 50 mg of 3-aminopropionitrile and 596 mg of 2-aminothiophenol in EtOH (15 mL) was heated at reflux for six h. After cooling the solution to room temperature, the reaction was concentrated and the residue was purified by silica gel chromatography to afford the title compound as a red oil. MS (M+H)+=179.1.

Preparation 25

N¹-(6-Methyl-5,6,7,8-tetrahydro-[1,6]naphthyridin-2-yl)-ethane-1,2-diamine

Step A

A solution of 250 mg of 2-chloro-5,6,7,8-tetrahydro-[1,6]naphthyridine (U.S. Pat. No. 6,169,093) in methylene chloride (6.1 mL) was treated with 0.148 mL of a 37% formalin solution, followed by 0.388 g of sodium triacetoxyborohydride. The reaction mixture was stirred at room temperature for 60 h and quenched by the addition of 2N sodium hydroxide (6 mL). After stirring for one h, the mixture was diluted with water and extracted with methylene chloride (2×). The organic layers were dried over sodium sulfate, filtered, and concentrated. Purification of the residue using silica gel chromatography provided N-methylchloronaphthyridine.

Step B

The product from Step A was dissolved in 10 equiv. of ethylenediamine and heated at 138° C. in a sealed tube for 18 h. The excess ethylenediamine was removed by distillation to provide the title compound as a brown oil. MS $(M+H)^+=207.0$.

Preparation 26

2-Amino-1-(7,8-dihydro-5H-[1,6]naphthyridin-6-yl)-ethanone

Step A

A solution of 90 mg of 2-chloro-5,6,7,8-tetrahydro-[1,6]naphthyridine hydrochloride (U.S. Pat. No. 6,169,093), 0.134 g of N-carbobenzyloxyglycine, 0.130 g of triethylamine, and 0.087 g of 1-hydroxy-7-azabenzotriazole in DMF (2.7 mL) at 0° C. was stirred as 0.123 g (0.640 mmol) of EDC was added. After two h, the reaction mixture was poured into 4% magnesium sulfate solution, and the resulting solution was extracted with EtOAc and then methylene chloride. The organic extracts were dried over sodium sulfate, filtered, and concentrated to give an oil that solidified upon standing. Trituration with MeOH and collection of the solids provided the desired amide intermediate.

Step B

To a solution of 93 mg (0.260 mmol) of the product from Step A in a 3:2 THF/MeOH mixture (5 mL) was added 100 mg of 10% Pd/C and 300 mg of cyclohexene. This mixture was heated to reflux for 16 h, cooled to room temperature, and filtered through a short pad of diatomaceous earth. The solids were washed with methylene chloride, and the filtrate was concentrated to provide the title compound. MS $(M+H)^+=192.1$.

Preparation 27

2-(4-Methyl-piperazin-1-yl)-ethylamine

Step A

A solution of 0.90 g of 4-methylpiperazine, 0.830 g of chloroacetonitrile, and 6.0 g of potassium carbonate in acetonitrile (9 mL) was stirred for 72 h. The reaction mixture was filtered and the filtrate was concentrated to provide a yellow solid.

Step B

The product from Step A was dissolved in a 1:1 mixture of ether/THF and was added to a suspension of 330 mg of LAH in ether (10 mL) at 0° C. The reaction was stirred at room temperature for 24 h, cooled to 0° C., and 5 mL of a solution of 6.0 N sodium hydroxide was added with stirring for 20 min. The solids were removed by filtration, and the filtrate was concentrated, dissolved in ether, dried over sodium sulfate, filtered, and concentrated to give the title compound as a light yellow oil. MS $(M+H)^+=144.1$.

Preparation 28

2-(3,4-Dihydro-1H-isoquinolin-2-yl)-ethylamine

Step A

A solution of 273 mg of methanesulfonic acid 2-benzyloxycarbonylamino-ethyl ester, 133 mg of 1,2,3,4-tetrahydroisoquinoline and 212 mg of sodium carbonate in DMF (3.0 mL) was heated to 90° C. for six h. The reaction mixture was cooled to room temperature, diluted with EtOAc, washed with water and saturated brine, dried over sodium sulfate, filtered, and concentrated. The residue was purified by silica gel chromatography to afford a yellow, oily product.

Step B

To a solution of 255 mg of the product from Step A in MeOH (3.0 mL) was added 99 mg of acetic acid, 102 mg of 10% Pd/C and 518 mg of ammonium formate. The mixture was refluxed for two h, cooled to room temperature, and filtered through a pad of diatomaceous earth. The filtrate was concentrated to give the title compound as a yellow oil. MS $(M+H)^+=177.2$.

The following 1,2-diamines were prepared in a manner analogous to that described in Preparation 28 using appropriate starting materials.

| Prep'n. | Name | MS $(M + H)^+$ |
|---|---|---|
| 29 | N¹-Methyl-N²-pyridin-2-ylmethyl-ethane-1,2-diamine | 164.9 |
| 30 | 2-(6,7-dimethoxy-3,4-dihydro-1H-isoquinolin-2-yl)-ethylamine | 237.2 |

Preparation 31

N¹-(4-Morpholin-4-ylmethyl-pyridin-2-yl)-ethane-1,2-diamine

Step A

A solution of 315 mg of 2-chloroisonicotinic acid and 209 mg of morpholine in EtOAc (4.0 mL) was stirred as 1.27 g of a 50% solution of 1-propanephosphonic acid cyclic anhydride was added. This mixture was stirred at room temperature for six h. and another 1.27 g of the anhydride was added followed by stirring for another 18 h. The reaction was poured into saturated sodium bicarbonate solution and extracted with EtOAc (3×). The organic layers were dried over sodium sulfate, filtered, and concentrated to provide the morpholine amide.

Step B

A mixture of 220 mg of the product from Step A was heated with 467 mg of tert-butyl-N-(2-aminoethyl)carbamate at 125° C. for 18 hrs. Diisopropylethylamine (371 mg) was added and heating was continued for 48 h. The reaction mixture was cooled to room temperature and purified by silica gel chromatography to provide the desired intermediate.

Step C

A solution of 155 mg of the product from Step B in THF (1.5 mL) and 0.66 mL of a 1.0 M solution of LAH in THF was heated at reflux for five h. The reaction was cooled to 0° C. and quenched by the sequential addition of 25 μL of water, 25 μL of 3.0 N NaOH, 75 μL of water, and solid sodium sulfate. The solids were removed by filtration and the filtrate was concentrated to leave a residue that was purified by silica gel chromatography to provide an oily product.

Step D

A solution of 50 mg of the product from Step C was dissolved in 10 equivalents of a 4.0 M solution of HCl in dioxane. This mixture was stirred for 90 min. and then concentrated to give the title compound as the hydrochloride salt. MS (M+H)$^+$=237.3.

The following 1,2-diamine was prepared in a manner analogous to that described in Preparation 31 using appropriate starting materials.

| Prep'n. | Name | MS (M + H)$^+$ |
|---|---|---|
| 32 | N$^1$-[4-(4-Methyl-piperazin-1-ylmethyl)-pyridin-2-yl]-ethane-1,2-diamine | 250.3 |

Preparation 33

2-(3,4-Dichloro-phenoxy)-ethylamine

A solution of 1.0 g of (2-hydroxy-ethyl)-carbamic acid tert-butyl ester, 0.96 g of 2,3-dichlorophenol, and 1.54 g of triphenylphosphine in THF (20 mL) was stirred as 1.19 g of diisopropyl azodicarboxylate was added. After stirring at ambient temperature for 72 h, the solvent was removed and the residue was dissolved in 10% sulfuric acid (10 mL) and warmed to 80° C. After 16 h, the reaction was cooled to ambient temperature and the mixture diluted with water and washed with EtOAc (2×). The organic layers were washed with water, and the pH of the combined aqueous layers was adjusted to 9 with 10 N NaOH solution. The mixture was extracted with chloroform (3×) and the combined organic layers were washed with sat. sodium chloride solution, dried over sodium sulfate, filtered and concentrated to provide the title compound as an orange oil. MS (M+H$^-$)=204.2.

The following aryloxy amines were prepared in a manner analogous to that described in Preparation 33 using appropriate starting materials.

| Prep'n. | Name | MS (M + H$^+$) or (M + H$^-$) |
|---|---|---|
| 34 | 2-(4-Chloro-3-fluoro-phenoxy)-ethylamine | 190.2 |
| 35 | 3-(2-Amino-ethoxy)-benzonitrile | 161.4 |
| 36 | 2-(3-Trifluoromethyl-phenoxy)-ethylamine | 206.4 |
| 37 | 2-(2-Methyl-pyridin-3-yloxy)-ethylamine | 153.2 |
| 38 | 2-(4-Chloro-phenoxy)-ethylamine | 172.5 |
| 39 | 2-(4-Bromo-phenoxy)-ethylamine | 216.5 |
| 40 | 2-(Pyridin-3-yloxy)-ethylamine | 329.4 |
| 41 | 2-(4-Chloro-2-methyl-phenoxy)-ethylamine | 374.4 |
| 42 | 2-(2-Methyl-phenoxy)-ethylamine | 342.4 |
| 43 | 2-(6-Methyl-pyridin-3-yloxy)-ethylamine | 343.5 |

Preparation 44

2-(Pyridin-2-yloxy)-ethylamine

A mixture of 500 mg of 2-aminoethanol and 328 mg of 60% sodium hydride-mineral oil dispersion in dioxane (27 mL) was heated to reflux for 30 min. After cooling to room temperature, 930 mg of 2-chloropyridine was added and the mixture was warmed to reflux and maintained at this temperature for 18 hrs. The reaction mixture was concentrated, diluted with water, and extracted with chloroform (3×). The organic extracts were washed with saturated brine, dried over sodium sulfate, filtered, concentrated, and the residue was purified by silica gel chromatography to give the title product as a yellow oily material. MS (M+H)$^+$=138.9.

Exemplary procedures for preparing the compounds of formula (I) according to Schemes 1-7 hereinabove are set forth in the following Examples.

EXAMPLE 1

6-tert-Butyl-8-(2-hydroxy-ethylamino)-2H-[1,2,4]triazolo[4,3-a]pyrazine-3-one

Step A

A suspension of 24.8 g of N-acetylcystine and 32.6 g of tert-butylhydrazine hydrochloride in EtOH (200 mL) was maintained at 0° C. while 19.8 g of ethyl cyanoformate was added slowly. After 15 min., 20.2 g of triethylamine was added dropwise over 15 min. and the temperature was maintained for three h. The reaction was diluted with methylene chloride and washed with sat. sodium bicarbonate solution (2×). The organic layer was dried over magnesium sulfate, filtered, and concentrated, and the residue was purified by silica gel chromatography to provide the amidrazone. MS (M+H$^+$)=188.3.

Step B

A solution of 15.8 g of the amidrazone of Step A in chloroform was cooled to 0° C. and 12.4 g of triphosgene was added in portions over 30 min. After stirring at ambient temperature for 18 h, the reaction mixture was poured into 300 mL of ice and 200 mL of sat. sodium bicarbonate solution. The organic layer was washed with sat. sodium bicarbonate solution, dried over magnesium sulfate, filtered, and concentrated. The residue was purified by silica get chromatography to afford 1-tert-butyl-5-oxo-4,5-dihydro-1H[1,2,4]triazole-3-carboxylic acid ethyl ester as a white solid. MS (M+H$^+$)=214.2.

Step C

A solution of 3.0 g of the product of Step B, 7.41 g of 1-bromo-3,3-dimethyl-2-butanone, and 4.15 g of lithium carbonate in a 2:1 mixture of acetonitrile/DMF (90 mL) was heated at 100° C. for four h. The reaction mixture was cooled to room temperature, diluted with EtOAc, and washed with sat. ammonium chloride solution. The aqueous layer was extracted with EtOAc and the combined organic layers were washed with sat. lithium chloride solution, dried over sodium sulfate, filtered, and concentrated. Purification by silica gel chromatography afforded 1-tert-butyl-4-(3,3-dimethyl-2-oxo-butyl)-5-oxo-4,5-dihydro-1H-[1,2,4]triazole-3-carboxylic acid ethyl ester as a yellow oil. MS (M+H$^+$)=312.3.

Step D

A solution of 8.60 g of the product of Step C and 21.30 g of ammonium acetate in MeOH was heated in a sealed system at 100° C. for 24 h. The solution was cooled to ambient temperature and concentrated to leave an oil that was partitioned between EtOAc and water. The aqueous layer was acidified to pH 5 with concentrated HCl and then extracted with EtOAc. The combined organic layers were washed with sat. sodium chloride, dried over sodium sulfate, filtered, and concentrated to provide 2,6-di-tert-butyl-2H,7H-[1,2,4]triazolo[4,3-a]pyrazine-3,8-dione as a white solid. MS (M+H$^+$)=265.3.

Step E

A solution of 5.90 g the product of Step D in phosphoryl chloride (100 mL) was heated to 110° C. After 16 h, the reaction mixture was cooled and the excess phosphoryl chloride was removed by distillation at reduced pressure (15 mm Hg). The residue was dissolved in chloroform and carefully poured onto 200 g of ice. After the ice had melted, the layers were separated and the aqueous was extracted with chloroform. The combined organic layers were washed with sat. sodium chloride solution, dried over sodium sulfate, filtered, and concentrated. The residue was purified by silica gel chromatography to yield 2-tert-butyl-8-chloro-6-tert-butyl-2H-[1,2,4]triazolo[4,3-a]pyrazin-3-one as a yellow solid. MS (M+H$^+$)=283.3.

Step F

A solution of 4.10 g of the product of Step E in 1,2-dichloroethane (142 mL) was treated with 5.60 g of aluminum trichloride and the suspension was heated to 80° C. After two h, the reaction mixture was cooled to ambient temperature and poured into ice water (500 g). After the ice had dissolved, the mixture was extracted with EtOAc and the organic layer was washed with sat. sodium chloride solution, dried over magnesium sulfate, filtered, and concentrated. The residue was purified by silica gel chromatography to afford 6-tert-butyl-8-chloro-2H-[1,2,4]triazolo[4,3-a]pyrazin-3-one as a yellow solid. MS (M+H$^+$)=227.3.

Step G

A solution of 0.50 g of the product of Step F and 0.40 g of ethanolamine in THF (6 mL) was heated at reflux for 16 h. After cooling the reaction mixture to ambient temperature, solvents were removed and the residue was purified by silica gel chromatography to yield the title compound as a white solid. MS (M+H$^+$)=252.3.

The following compounds were prepared in a manner analogous to that described in Example 1 using appropriate starting materials.

| Example | Name | MS (M + H)$^+$ |
|---|---|---|
| 2 | 6-tert-Butyl-8-isopropylamino-2H-[1,2,4]triazolo[4,3-a]pyrazin-3-one | 328.3 |
| 3 | 6-tert-Butyl-8-(2-pyridin-3-yl-ethylamino)-2H-[1,2,4]triazolo[4,3-a]pyrazin-3-one | 313.4 |

The following compounds of formula (I) were prepared in a manner analogous to that described in Example 1, Steps A to E, using appropriate reactants.

| Example | Name | MS (M + H$^+$) or (M + H$^-$) |
|---|---|---|
| 4 | 2-tert-Butyl-8-chloro-6-(4-chloro-phenyl)-2H-[1,2,4]triazolo[4,3-a]pyrazin-3-one | 337.3 (+) |
| 5 | 2-tert-Butyl-8-chloro-6-(3-bromo-phenyl)-2H-[1,2,4]triazolo[4,3-a]pyrazin-3-one | 381.2 (+) |
| 6 | 3-(2-tert-Butyl-8-chloro-6-(2-chloro-phenyl)-2H-[1,2,4]triazolo[4,3-a]pyrazin-6-yl)-benzonitrile | 337.3 (+) |
| 7 | 3-(2-tert-Butyl-8-chloro-3-oxo-2,3-dihydro-[1,2,4]triazolo[4,3-a]pyrazin-6-yl)-benzoic acid methyl ester | 361.3 (+) |
| 8 | 2-(2-tert-Butyl-8-chloro-3-oxo-2,3-dihydro-[1,2,4]triazolo[4,3-a]pyrazin-6-yl)-2-methyl-propionic acid methyl ester | 327.3 (+) |
| 9 | 1-(2-tert-Butyl-8-chloro-3-oxo-2,3-dihydro-[1,2,4]triazolo[4,3-a]pyrazin-6-yl)-cyclopentanecarboxylic acid ethyl ester | 367.2 (−) |
| 10 | 2,6-Di-tert-butyl-8-chloro-5-methyl-2H-[1,2,4]triazolo[4,3-a]pyrazin-3-one | 297.2 (+) |
| 11 | 2,6-Di-tert-butyl-8-chloro-5-m-tolyl-2H-[1,2,4]triazolo[4,3-a]pyrazin-3-one | 315.1 (+) |
| 12 | 2-tert-Butyl-8-chloro-6-isopropyl-5-phenyl-2H-[1,2,4]triazolo[4,3-a]pyrazin-3-one | 345.3 (+) |
| 13 | 2-tert-Butyl-8-chloro-6-isopropyl-5-methyl-2H-[1,2,4]triazolo[4,3-a]pyrazin-3-one | 283.3 (+) |
| 14 | 2-tert-Butyl-8-chloro-5-(3,5-dimethoxy-phenyl)-6-isopropyl-2H-[1,2,4]triazolo[4,3-a]pyrazin-3-one | 405.4 (+) |

-continued

| Example | Name | MS (M + H⁺) or (M + H⁻) |
|---------|------|-------------------------|
| 15 | 2-tert-Butyl-8-chloro-5,6-dimethyl-2H-[1,2,4]triazolo[4,3-a]pyrazin-3-one | 255.1 (+) |

The following compound of formula (I) was prepared in a manner analogous to that described in Example 1, Steps A to E, using appropriate reactants.

| Example | Name | MS (M + H⁺) or (M + H⁻) |
|---------|------|-------------------------|
| 16 | 2,6-Di-tert-butyl-8-chloro-5-phenyl-2H-[1,2,4]triazolo[4,3-a]pyrazin-3-one | 315.1 (−) |

EXAMPLE 17

6-tert-Butyl-8-(piperidin-4-ylamino)-2H-[1,2,4]triazolo[4,3-a]pyrazin-3-one

Step A

A solution of 40 mg of 2-tert-butyl-8-chloro-6-(3-bromophenyl)-2H-[1,2,4]triazolo[4,3-a]pyrazin-3-one, 31 mg of $N^1$-(4-trifluoromethyl-pyridin-2-yl)-ethane-1,2-diamine and 22 mg of diisopropylethylamine in THF (1.0 mL) was heated to reflux. After 16 h, the reaction was concentrated and the residue purified by silica gel chromatography to provide 6-(3-bromo-phenyl)-2-tert-butyl-8-[2-(4-trifluoromethyl-pyridin-2-ylamino)-ethylamino]-2H-[1,2,4]triazolo[4,3a]pyrazin-3-one as a white solid. MS (M+H⁺)=550.3.

Step B

A solution of 40 mg of the compound of Step A in dichloroethane (1.0 mL) was treated with 176 mg of boron trichloride and the mixture was heated in a sealed tube at 126° C. for 16 h. The reaction was cooled to ambient temperature and the excess boron trichloride carefully quenched by the addition of water. The mixture was extracted with chloroform and the organic layer was washed with sat. sodium chloride solution, dried over sodium sulfate, filtered, and concentrated. The residue was purified by silica gel chromatography to afford the title compound as a white solid. MS (M+H⁺)=494.2.

The following examples were prepared in a manner analogous to that described in Example 17 using appropriate starting materials in the presence of either boron trichloride or boron tribromide.

| Example | Name | MS (M + H)⁺ |
|---------|------|-------------|
| 18 | 6-(4-Chloro-phenyl)-8-isopropylamino-2H-[1,2,4]triazolo[4,3-a]pyrazin-3-one | 304.3 |
| 19 | 6-tert-Butyl-8-(2,2-dimethyl-propylamino)-2H-[1,2,4]triazolo[4,3-a]pyrazin-3-one | 278.4 |

EXAMPLE 20

8-[2-(Benzothiazol-2-ylamino)-ethylamino]-6-(4-chloro-phenyl)-2H-[1,2,4]triazolo[4,3-a]pyrazin-3-one Step A A solution of 335 mg of 2-tert-butyl-8-chloro-6-(4-chlorophenyl)-2H-[1,2,4]triazolo[4,3-a]pyrazin-3-one in 1,2-dichloroethane (10.0 mL) was treated with 2.35 g of boron tribromide and the solution was heated to 125° C. in a sealed tube. After two h, the reaction was cooled to ambient temperature and the excess boron reagent was carefully destroyed by the careful addition of water. The reaction mixture was basified with 2N NaOH to pH 9 and then acidified with sat. ammonium chloride solution. The aqueous layer was extracted with EtOAc and the organic layers were washed with sat. sodium chloride solution, dried over sodium sulfate, filtered, and concentrated to provide 8-bromo-6-(4-chloro-phenyl)-2H-[1,2,4]triazolo[4,3-a]pyrazin-3-one as a tan solid. MS (M+H⁺)=438.3.

Step B

A solution of 50 mg of the product of Step A, 43 mg of $N^1$-benzothiazol-2-yl-ethane-1,2-diamine, and 124 mg of triethylamine in THF (1.0 mL) was heated to reflux. After 16 h, the reaction mixture was cooled to ambient temperature and then partitioned between EtOAc and water. The organic layer was dried over sodium sulfate, filtered, and concentrated to a residue that was purified by silica gel chromatography to afford the title compound as a white solid. MS (M+H⁺)= 438.3.

The following compounds of formula (I) were prepared in a manner analogous to that described in Example 20 using appropriate starting materials.

| Example | Name | MS (M + H⁺) or (M + H⁻) |
|---------|------|-------------------------|
| 21 | 6-(3-Bromo-phenyl)-8-isopropylamino-2H-[1,2,4]triazolo[4,3-a]pyrazin-3-one | 348.3 (+) |
| 22 | 6-(4-Chloro-phenyl)-8-[2-(4-trifluoromethyl-pyridin-2-ylamino)-ethylamino]-2H-[1,2,4]triazolo[4,3-a]pyrazin-3-one | 450.3 (+) |
| 23 | 3-[8-(1-Ethyl-propylamino)-3-oxo-2,3-dihydro-[1,2,4]triazolo[4,3-a]pyrazin-6-yl]-benzonitrile | 323.2 (+) |

-continued

| Example | Name | MS (M + H⁺) or (M + H⁻) |
|---|---|---|
| 24 | 3-(8-Cyclopentylamino-3-oxo-2,3-dihydro-[1,2,4]triazolo[4,3-a]pyrazin-6-yl)-benzonitrile | 321.2 (+) |
| 25 | 3-[8-(2,2-Dimethyl-propylamino)-3-oxo-2,3-dihydro-[1,2,4]triazolo[4,3-a]pyrazin-6-yl]-benzonitrile | 323.2 (+) |
| 26 | 3-[8-(3-Hydroxy-2,2-dimethyl-propylamino)-3-oxo-2,3-dihydro-[1,2,4]triazolo[4,3-a]pyrazin-6-yl]-benzonitrile | 339.2 (+) |
| 27 | 3-(8-Isopropylamino-3-oxo-2,3-dihydro-[1,2,4]triazolo[4,3-a]pyrazin-6-yl)-benzoic acid methyl ester | 328.3 (+) |
| 28 | 8-[2-(Benzothiazol-2-ylamino)-ethylamino]-6-tert-butyl-2H-[1,2,4]triazolo[4,3-a]pyrazin-3-one | 384.3 (+) |
| 29 | 6-tert-Butyl-8-[2-(4-trifluoromethyl-pyridin-2-ylamino)-ethylamino]-2H-[1,2,4]triazolo[4,3-a]pyrazin-3-one | 396.4 (+) |
| 30 | 6-tert-Butyl-8-(2-piperidin-1-yl-ethylamino)-2H-[1,2,4]triazolo[4,3-a]pyrazin-3-one | 319.4 (+) |
| 31 | 6-tert-Butyl-8-[3-(4-methyl-piperazin-1-yl)-propylamino]-2H-[1,2,4]triazolo[4,3-a]pyrazin-3-one | 348.4 (+) |
| 32 | 6-tert-Butyl-8-[(1-ethyl-pyrrolidin-2-ylmethyl)-amino]-2H-[1,2,4]triazolo[4,3-a]pyrazin-3-one | 319.4 (+) |
| 33 | 6-tert-Butyl-8-(2-pyrrolidin-1-yl-ethylamino)-2H-[1,2,4]triazolo[4,3-a]pyrazin-3-one | 305.4 (+) |
| 34 | 6-tert-Butyl-8-[2-(1-methyl-pyrrolidin-2-yl)-ethylamino]-2H-[1,2,4]triazolo[4,3-a]pyrazin-3-one | 319.4 (+) |
| 35 | 4-[2-(6-tert-Butyl-3-oxo-2,3-dihydro-[1,2,4]triazolo[4,3-a]pyrazin-8-ylamino)-ethyl]-benzenesulfonamide | 391.3 (+) |
| 36 | 6-tert-Butyl-8-[2-(2-methyl-5-nitro-imidazol-1-yl)-ethylamino]-2H-[1,2,4]triazolo[4,3-a]pyrazin-3-one | 361.4 (+) |
| 37 | 6-tert-Butyl-8-(2-morpholin-4-yl-ethylamino)-2H-[1,2,4]triazolo[4,3-a]pyrazin-3-one | 321.3 (+) |
| 38 | 5,6-Dimethyl-8-(3-morpholin-4-yl-propylamino)-2H-[1,2,4]triazolo[4,3-a]pyrazin-3-one | 307.2 (+) |
| 39 | 5,6-Dimethyl-8-(2-pyridin-3-yl-ethylamino)-2H-[1,2,4]triazolo[4,3-a]pyrazin-3-one | 285.1 (+) |
| 40 | 6-tert-Butyl-5-methyl-8-(3-morpholin-4-yl-propylamino)-2H-[1,2,4]triazolo[4,3-a]pyrazin-3-one | 349.3 (+) |
| 41 | 6-tert-Butyl-5-methyl-8-(2-pyridin-3-yl-ethylamino)-2H-[1,2,4]triazolo[4,3-a]pyrazin-3-one | 327.2 (+) |

EXAMPLE 42

2-(8-Isopropylamino-3-oxo-2,3-dihydro-[1,2,4]triazolo[4,3-a]pyrazin-6-yl)-N-phenethyl-isobutyramide Step A A solution of 215 mg of 2-(2-tert-butyl-8-chloro-3-oxo-2,3-dihydro-[1,2,4]triazolo[4,3-a]pyrazin-6-yl)-2-methyl-propionic acid methyl ester and 388 mg of isopropylamine in THF (5.0 mL) was heated at reflux for 2 h. The reaction mixture was cooled to ambient temperature, diluted with water and extracted with EtOAc. The organic extract was dried over sodium sulfate, filtered, and concentrated to provide 2-(2-tert-butyl-8-isopropylamino-3-oxo-2,3-dihydro-[1,2,4]triazolo[4,3-a]pyrazin-6-yl)-2-methyl-propionic acid methyl ester as a light yellow solid. MS (M+H⁺)=350.4.

Step B

A solution of 160 mg of the product of Step A in 1,4-dioxane (5.0 mL) and 6N NaOH (1.0 mL) was warmed to 50° C. After three days, the solvents were removed and the residue was dissolved in water and extracted with chloroform. The pH of the aqueous layer was adjusted to 3 with 2N HCl and then extracted with 9:1 chloroform/IPA (3×). The organic extracts were washed with sat. sodium chloride solution, dried over sodium sulfate, filtered, and concentrated to afford 2-(2-tert-butyl-8-isopropylamino-3-oxo-2,3-dihydro-[1,2,4]triazolo[4,3-a]pyrazin-6-yl)-2-methyl-propionic acid as a white solid. MS (M+H⁺)=336.4.

Step C

A solution of 45 mg of the product of Step B, 31 mg of 2-phenethylamine, 65 mg of triethylamine, and 248 mg of 1-propanephosphonic acid cyclic anhydride in EtOAc (2.0 mL) was warmed to 80° C. After 16 h, the reaction was poured into water and extracted with EtOAc. The organic layer was washed with sat. sodium chloride solution, dried over sodium sulfate, filtered, and concentrated. The residue was purified by silica gel chromatography to afford 2-(2-tert-butyl-8-isopropylamino-3-oxo-2,3-dihydro-[1,2,4]triazolo[4,3a]pyrazin-6-yl)-N-phenethyl-isobutyramide as a white solid. MS (M+H⁺)=439.5.

Step D

A solution of 48 mg of the product of Step C and 276 mg of boron tribromide in dichloroethane (2.0 mL) was heated in a sealed tube at 125° C. After two h, the reaction was cooled to ambient temperature and the excess reagent carefully quenched by the addition of water. The resulting mixture was extracted with EtOAc and the organic layer washed with sat. sodium chloride, dried over sodium sulfate, filtered, and concentrated. The residue was purified by silica gel chromatography to afford the title compound as a tan solid. MS (M+H⁺)= 383.4.

The following example was prepared in a manner analogous to that described in Example 42 using appropriate starting materials.

| Example | Name | MS (M + H)+ |
|---|---|---|
| 43 | 2-(8-Isopropylamino-3-oxo-2,3-dihydro-[1,2,4]triazolo[4,3-a]pyrazin-6-yl)-N-(3-phenyl-prop-2-ynyl)-isobutyramide | 393.4 |

EXAMPLE 44

6-Isopropyl-8-isopropylamino-2H-[1,2,4]triazolo[4,3-a]pyrazin-3-one

Step A

To a solution of 400 mg of methyl 2-(2-tert-butyl-8-isopropylamino-3-oxo-2,3-dihydro-[1,2,4]triazolo[4,3-a]pyrazin-6-yl)-2-methyl-propionate in dioxane (10.0 mL) was added 6.0 N KOH (1.0 mL) and the mixture was heated at reflux for 16 h. The reaction mixture was cooled to ambient temperature, diluted with water, the pH was adjusted to 2.0 with 6.0 N HCl, and the mixture was extracted with EtOAc (2×). The organic extracts were dried over magnesium sulfate, filtered, and concentrated to leave 2-(2-tert-butyl-8-isopropylamino-3-oxo-2,3-dihydro-[1,2,4]triazolo[4,3-a]pyrazin-6-yl)-2-methyl-propionic acid as a white solid. MS (M+H+)=336.3.

Step B

A solution of 300 mg of the product of Step A in AcOH (5.0 mL) was heated at reflux for two h. The solvent was removed to afford 2-tert-butyl-6-isopropyl-8-isopropylamino-2H-[1,2,4]triazolo[4,3-a]pyrazin-3-one as a light green solid. A suspension of 240 mg of this product and 329 mg of aluminum trichloride in dichloroethane (10.0 mL) was heated at reflux for two h. The reaction was poured into water and the resulting solution was extracted with EtOAc. The organic extract was dried over magnesium sulfate, filtered, and concentrated and the residue was purified by silica gel chromatography to afford the title compound as an off-white solid. MS (M+H+)= 234.1.

EXAMPLE 45

3-(8-Isopropylamino-3-oxo-2,3-dihydro-[1,2,4]triazolo[4,3-a]pyrazin-6-yl)-N-phenethyl-benzamide Step A A solution of 580 mg of 3-(2-tert-butyl-8-chloro-3-oxo-2,3-dihydro-[1,2,4]triazolo[4,3-a]pyrazin-6-yl)-benzoic acid methyl ester and 944 mg of isopropylamine in THF (8.0 mL) was stirred at ambient temperature. After 72 h, the reaction was diluted with EtOAc and washed with water followed by sat. sodium chloride solution. The organic layer was dried over sodium sulfate, filtered, and concentrated to an orange semi-solid. This material was dissolved in 1,4-dioxane (6.0 mL) and 2N KOH (1.0 mL) was added. This mixture was heated at reflux for 16 h, cooled to ambient temperature and the solvent removed. The residue was dissolved in water and the pH adjusted to 3 with 2N HCl prior to extraction with 9:1 chloroform/MeOH (3×). The organic extracts were washed with sat. sodium chloride solution, dried over sodium sulfate, filtered, and concentrated to leave 3-(2-tert-butyl-8-isopropylamino-3-oxo-2,3-dihydro-[1,2,4]triazolo[4,3-a]pyrazin-6-yl)-benzoic acid as a yellow solid. MS (M+H+)=370.4.

Step B

A solution of 50 mg of the product of Step A, 33 mg of phenethylamine, 68 mg of triethylamine and 258 mg of 1-propanephosphonic acid cyclic anhydride in EtOAc (3.0 mL) was warmed to 80° C. The organic layer was washed with sat. sodium chloride solution, dried over sodium sulfate, filtered, and concentrated. The residue was purified by silica gel chromatography to afford 3-(2-tert-butyl-8-isopropylamino-3-oxo-2,3-dihydro-[1,2,4]triazolo[4,3-a]pyrazin-6-yl)-N-phenethyl-benzamide as a white solid. MS (M+H+)=473.4.

Step C

A solution of 32 mg of the product of Step B and 251 mg of boron tribromide in dichloroethane (2.0 mL) was heated in a sealed tube at 125° C. After two h, the reaction was cooled to ambient temperature and the excess reagent carefully quenched by the addition of water. The resulting mixture was extracted with EtOAc and the organic layer washed with sat. sodium chloride, dried over sodium sulfate, filtered, and concentrated. The residue was purified by silica gel chromatography to afford the title compound as a tan solid. MS (M+H+)= 417.4.

The following examples were prepared in a manner analogous to that described in Example 45 using appropriate starting materials.

| Example | Name | MS (M + H)+ |
|---|---|---|
| 46 | 3-(8-Isopropylamino-3-oxo-2,3-dihydro-[1,2,4]triazolo[4,3-a]pyrazin-6-yl)-N-(2-pyridin-2-yl-ethyl)-benzamide | 418.4 |
| 47 | 3-(8-Isopropylamino-3-oxo-2,3-dihydro-[1,2,4]triazolo[4,3-a]pyrazin-6-yl)-N-(2-pyridin-4-yl-ethyl)-benzamide | 418.3 |

EXAMPLE 48

1-(8-Isopropylamino-3-oxo-2,3-dihydro-[1,2,4]triazolo[4,3-a]pyrazin-yl-cyclopentanecarboxlic acid Step A A solution of 365 mg of 1-(2-tert-butyl-8-chloro-3-oxo-2,3-dihydro-[1,2,4]triazolo[4,3-a]pyrazin-6-yl)-cyclopentanecarboxylic acid ethyl ester and 590 mg of isopropylamine in THF (5.0 mL) was heated at reflux for two h. The solvent was removed and the residue was purified by silica gel chromatography to afford 1-(2-tert-butyl-8-isopropylamino-3-oxo-2,3-dihydro-[1,2,4]triazolo[4,3-a]pyrazin-6-yl)-cyclopentanecarboxylic acid ethyl ester as an oil. MS (M+H+)=390.3.

Step B

A solution of 400 mg of the product of Step A in 1,4-dioxane (10 mL) was treated with 6N KOH (2.0 mL) and the mixture was heated at 60° C. for three h. The reaction was cooled to ambient temperature, diluted with water, and the pH adjusted to 2 with 2N HCl. The mixture was extracted with EtOAc and the organic layer was dried over MgSO4, filtered, and concentrated to afford 1-(2-tert-butyl-8-isopropylamino-3-oxo-2,3-dihydro-[1,2,4]triazolo[4,3-a]pyrazin-6-yl)-cyclopentanecarboxylic acid as a white solid. MS (M+H+)= 360.3.

Step C

A solution of 300 mg of the product of Step B and 440 mg of aluminum trichloride in dichloroethane (4.0 mL) was shaken together at 80° C. for one h. The reaction was cooled to ambient temperature and the reaction quenched by the addition of ice water. The mixture was extracted with EtOAc (2×) and the combined organic extracts were washed with sat. sodium chloride solution, dried over magnesium sulfate, filtered, and concentrated. The residue was purified using a Shimadzu reverse-phase HPLC (Shimadzu LC-8A Preparatory LC, Shimadzu Scientific Instrument Inc. USA, 7102 Riverwood Dr., Columbia, Md.; Waters symmetry 30×50 column, solvent gradient=15-100% acetonitrile/1% aqueous formic acid; 40 mL/min.) system to afford the title compound as a white solid. MS (M+H$^+$)=306.2.

EXAMPLE 49

6-Cyclopentyl-8-isopropylamino-2H-[1,2,4]triazolo[4,3-a]pyrazin-3-one

A solution of 20 mg of 1-(8-isopropylamino-3-oxo-2,3-dihydro-[1,2,4]triazolo[4,3-a]pyrazin-6-yl)-cyclopentanecarboxylic acid in AcOH (3.0 mL) was warmed to 120° C. for 30 min. The reaction was cooled to ambient temperature and diluted with water. The mixture was extracted with EtOAc, the organic layer was washed with water (2×), dried over magnesium sulfate, filtered, and concentrated to leave the title compound as a tan solid. MS (M+H$^+$)=262.3.

EXAMPLE 50

8-Chloro-5-phenyl-2H-[1,2,4]triazolo[4,3-a]pyrazin-3-one

Step A

A solution of 1.0 g of 3-bromo-5-phenyl-pyrazin-2-ol (J. Het. Chem., 665 (1978)) in phosphorous oxychloride (10 mL) was heated at reflux for four h and then at ambient temperature for 48 h. The reaction was carefully poured onto 200 g of ice followed by the addition of 5N NaOH solution (100 mL). The resulting solution was neutralized by the addition of potassium dihydrogen phosphate and then extracted with chloroform (3×). The organic layers were dried over sodium sulfate, filtered, and concentrated. The residue was purified by silica gel chromatography to afford 2,3-dichlorophenyl-6-phenyl-pyrazine as a yellow solid. MS (M+H$^+$)=226.1.

Step B

A solution of 20.0 g of the product of Step A in IPA (134 mL) was treated with 8.58 g of anhydrous hydrazine. The mixture was heated at reflux for two h and then cooled to ambient temperature and concentrated to dryness. The solid residue was dissolved in methylene chloride, washed with sat. sodium chloride solution, dried over sodium sulfate, filtered, and concentrated to a tan solid. Purification by silica gel chromatography provided equal quantities of (3-chloro-5-phenyl-pyrazin-2-yl)-hydrazine and (3-chloro-6-phenyl-pyrazin-2-yl)-hydrazine as yellow solids. A solution of 219 mg of (3-chloro-6-phenyl-pyrazin-2-yl)-hydrazine and 324 mg of CDI in THF (10 mL) was stirred at ambient temperature for 4 h. The solvent was removed and he residue was partitioned between EtOAc/water and the organic layer was dried over magnesium sulfate, filtered, and concentrated to provide 8-chloro-6phenyl-2H-[1,2,4]triazolo[4,3-a]pyrazin-3-one as a light yellow solid. MS (M+H$^-$)=245.7.

EXAMPLE 51

8-Isopropylamino-5-phenyl-2H-[1,2,4]triazolo[4,3-a]pyrazin-3-one

A solution of 90 mg of 8-chloro-6-phenyl-2H-[1,2,4]triazolo[4,3-a]pyrazin-3-one, 64 mg of isopropylamine and 73 mg of TEA in THF (10 mL) was stirred at ambient temperature for one h and then heated at reflux for 16 h. The solvent was removed and the residue was dissolved in water and the pH adjusted to 2.0 with 2.0 N HCl. The solid was collected and triturated with acetone to provide the title compound as a light tan solid. MS (M+H$^-$)=269.2.

The following compound was prepared in a manner analogous to that described in Example 51 using appropriate starting materials.

| Example | Name | MS (M + H$^-$) |
|---|---|---|
| 52 | 5-Phenyl-8-(2-pyridin-3-yl-ethylamino)-2H-[1,2,4]triazolo[4,3-a]pyrazin-3-one | 332.3 |

EXAMPLE 53

8-Isopropylamino-6-phenyl-2H-[1,2,4]triazolo[4,3-a]pyrazin-3-one

Step A

A mixture of 15.3 g of NaH (60% suspension in mineral oil) and 80.0 g of 3-bromo-5-phenyl-pyrazin-2-ol (J Het. Chem., 665 (1978)) was stirred together for 15 min. After gas evolution ceased, 90.0 g of trifluoromethanesulfonic anhydride was added dropwise over one h. The mixture was stirred an additional 30 min. and was filtered through a pad of silica gel and the solids were washed with methylene chloride. Concentration of the filtrate provided 3-bromo-5-phenyl-pyrazin-2-trifluoromethansulfonate that was dissolved in IPA (200 mL) and stirred as 4.48 g of hydrazine was added. The mixture was stirred at ambient temperature for 16 h. The resulting solid was collected, washed with methylene chloride, and dried under reduced pressure. The filtrate was resubjected to the above reaction conditions a second and third time to provide (3-bromo-5-phenyl-pyrazin-2-yl)-hydrazine as the trifluoromethane sulfonate salt. A solution of 265 mg of (3-bromo-5-phenyl-pyrazin-2-yl)-hydrazine trifluoromethane sulfonate in THF (5.0 mL) was stirred as 243 mg of CDI was added in portions over 15 min. The resulting solution was stirred for 1.5 h and was diluted with EtOAc and washed with water. The organic layer was dried over magnesium sulfate, filtered, and concentrated to provide 8-bromo-6-phenyl-2H-[1,2,4]triazolo[4,3-a]pyrazin-3-one as a tan solid. MS (M+H$^-$)=290.2.

Step B

A solution of 29 mg of the product of Step A and 118 mg of isopropylamine in THF (5.0 mL) was heated at reflux for 16 h. The reaction was concentrated to one-quarter volume, diluted with water, and the pH was adjusted to pH 2 with 2N HCl. The solid was collected and triturated for one h in isopropyl ether at 60° C. before being collected and dried to give the title compound as a tan solid. MS (M+H$^+$)=270.1.

The following examples were prepared in a manner analogous to that described in Example 53 using appropriate starting materials.

| Example | Name | MS (M + H)⁺ |
|---|---|---|
| 54 | 6-Phenyl-8-[2-(5-trifluoromethyl-pyridin-2-ylamino)-ethylamino]-2H-[1,2,4]triazolo[4,3-a]pyrazin-3-one | 414.2 |
| 55 | 8-[2-(1H-Indol-3-yl)-ethylamino]-6-phenyl-2H-[1,2,4]triazolo[4,3-a]pyrazin-3-one | 369.2 |

EXAMPLE 56

8-Isopropylamino-3-oxo-2,3-dihydro-[1,2,4]triazolo[4,3-a]pyrazine-6-carboxylic acid Step A To a stirred solution of 7.1 g of (3-chloro-pyrazin-2-yl)-hydrazine hydrochloride (J. Org. Chem., 29, 3452 (1968)), in $CH_2Cl_2$ at 0° C. was slowly added 21.0 g of trifluoroacetic anhydride. The reaction was warmed to ambient temperature over 30 min. and then poured into water. The layers were separated and the aqueous layer was extracted with methylene chloride. The combined organic layers were washed with water, dried over magnesium sulfate, filtered, and concentrated and the residue was purified by silica gel chromatography to afford trifluoroacetic acid N'-(3-chloro-pyrazin-2-yl)-hydrazide as a yellow solid. MS (M+H⁺)=241.2.

Step B

A solution of 2.40 g of the product of Step A and 1.97 g of pyridine in AcOH (10.0 mL) at 0° C. was stirred as a solution of 1.92 g of bromine in AcOH (1.0 mL) was added dropwise. The resulting mixture was stirred at 0° C. for one h and then warmed to ambient temperature and stirred for an additional 16 h. The reaction mixture was poured into water and extracted with EtOAc (2×). The combined organic extracts were washed with water, dried over magnesium sulfate, filtered, and concentrated to an oil that was purified by silica gel chromatography to provide trifluoroacetic acid N'-(5-bromo-3-chloro-pyrazin-2-yl)-hydrazide as a white solid. MS (M+H⁺)=320.1.

Step C

To a solution of 512 mg of the product of Step B in EtOH (8.0 mL) was added concentrated HCl (1.0 mL) and the mixture was heated at reflux. After four h, the reaction was concentrated to dryness and the residue was dissolved in water and the pH adjusted to 8 with sat. sodium bicarbonate solution. The mixture was extracted with EtOAc (2×) and the organic extracts were dried over magnesium sulfate, filtered, and concentrated to provide (5-bromo-3-chloro-pyrazin-2-yl)-hydrazine as a light yellow solid. MS (M+H⁺)=224.2.

Step D

A solution of 2.50 g of the product of Step C in THF (60 mL) was stirred as 3.32 g of triphosgene was added in portions to provide a tan suspension. A homogeneous solution was obtained after 30 min. and the excess phosgene was destroyed by the careful addition of water and the mixture was extracted with EtOAc. The organic extracts were washed with sat. sodium chloride solution, dried over magnesium sulfate, filtered, and concentrated to afford 6-bromo-8-chloro-2H-[1,2,4]triazolo[4,3-a]pyrazin-3-one as a light yellow solid. MS (M+H⁻)=280.1.

Step E

A solution of 0.50 g of the product of Step D and 0.59 g of isopropylamine in THF (20 mL) was heated to reflux. After one h, the reaction was concentrated and the residue partitioned between EtOAc and water. The layers were separated and the organic phase was washed with sat sodium chloride solution, dried over magnesium sulfate, filtered, and concentrated to provide 6-bromo-8-isopropylamino-2H-[1,2,4]triazolo[4,3-a]pyrazin-3-one as a light tan solid. MS (M+H⁻)=271.2.

Step F

A solution of 521 mg of the product of Step E, 313 mg of 1,3-bis-(diphenylphosphino)propane, 212 mg of palladium (II) acetate and 13.8 g of TEA in a 10:1 mixture of MeOH/DMSO (209 mL) was agitated under a carbon monoxide atmosphere (45 psi) at 75° C. After 14 h, the reaction was cooled to ambient temperature and portioned between EtOAc/water. The resulting mixture was filtered through a pad of diatomaceous earth and the solids washed with EtOAc. The layers were separated and the aqueous was extracted with EtOAc. The combined organic extracts were washed with sat. sodium chloride solution, dried over magnesium sulfate, filtered, and concentrated to provide 8-isopropylamino-3-oxo-2,3-dihydro-[1,2,4]triazolo[4,3-a]pyrazine-6-carboxylic acid methyl ester as an oil. MS (M+H⁺)=252.3.

Step G

A solution of 720 mg of the product of Step F in dioxane (10 mL) was treated with 6N KOH (2.0 mL) and the mixture was stirred at ambient temperature. After six h, the pH of the reaction was adjusted to 4.0 with concentrated HCl and the mixture was extracted with 3:1 chloroform/IPA (3×). The combined organic extracts were dried over magnesium sulfate, filtered, and concentrated to provide 8-isopropylamino-3-oxo-2,3-dihydro-[1,2,4]triazolo[4,3-a]pyrazine-6-carboxylic acid as a tan solid. MS (M+H⁺)=236.0.

EXAMPLE 57

8-Isopropylamino-3-oxo-2,3-dihydro-[1,2,4]triazolo[4,3-a]pyrazine-6-carboxylic acid phenethyl-amide A solution of 272 mg of 6-bromo-8-isopropylamino-2H-[1,2,4]triazolo[4,3-a]pyrazin-3-one, 206 mg of 1,3-bis-(diphenylphosphino)propane, 67 mg of palladium(II) acetate and 2.40 g of phenethylamine in a 10:1 mixture of DMSO/TEA was agitated under a carbon monoxide atmosphere (40 psi) at 70° C. After four h, the reaction was cooled to ambient temperature and the solids were removed by filtration through a pad of diatomaceous earth. The filtrate was poured into water and extracted with EtOAc (2×). The organic extracts were washed with water, sat. sodium chloride solution, dried over magnesium sulfate, filtered, and concentrated. The residue was purified by silica gel chromatography to provide the title compound as a light yellow solid. MS (M+H⁺)=339.3.

The following compounds were prepared in a manner analogous to that described in Example 57 using appropriate starting materials.

| Example | Name | MS (M + H⁻) |
|---|---|---|
| 58 | 8-Isopropylamino-3-oxo-2,3-dihydro-[1,2,4]triazolo[4,3-a]pyrazine-6-carboxylic acid (2-pyridin-2-yl-ethyl)-amide | 340.2 |
| 59 | 8-Isopropylamino-6-(piperidine-1-carbonyl)-2H-[1,2,4]triazolo[4,3-a]pyrazin-3-one | 303.2 |
| 60 | 8-Isopropylamino-3-oxo-2,3-dihydro-[1,2,4]triazolo[4,3-a]pyrazine-6-carboxylic acid methyl-phenethyl-amide | 353.2 |
| 61 | 6-(4-Benzyl-piperazine-1-carbonyl)-8-isopropylamino-2H-[1,2,4]triazolo[4,3-a]pyrazin-3-one | 394.3 |
| 62 | 8-Isopropylamino-3-oxo-2,3-dihydro-[1,2,4]triazolo[4,3-a]pyrazine-6-carboxylic acid benzylamide | 325.2 |

EXAMPLE 63

6-tert-Butyl-8-(2-pyridin-3-yl-ethylamino)-5-m-tolyl-2H-[1,2,4]triazolo[4,3-a]pyrazin-3-one Step A A suspension of 440 mg of 2,6-di-tert-butyl-8-chloro-5-o-tolyl-2H-[1,2,4]triazolo[4,3-a]pyrazin-3-one and 504 mg of aluminum trichloride in dichloroethane (12.0 mL) was heated to 100° C. After one h, the reaction was cooled to ambient temperature and the excess aluminum reagent was quenched by the careful addition of water. This mixture was diluted with chloroform and the layers were separated. The organic layer was washed with water and then sat. sodium chloride solution, dried over sodium sulfate, filtered, and concentrated. The residue was purified by silica gel chromatography to afford 6-tert-butyl-8-chloro-5-o-tolyl-2H-[1,2,4]triazolo[4,3-a]pyrazin-3-one as a yellow solid. MS (M+H⁻)=315.1.

Step B

A solution of 31 mg of the product of Step A and 120 mg of 2-pyridin-3-yl-ethylamine in THF (3.0 mL) was heated at reflux for 16 h. The solvent was removed and the residue was purified by silica gel chromatography to afford the title compound as a light yellow solid. MS (M+H⁺)=403.4.

The following examples were prepared in a manner analogous to that described in Example 63 using appropriate starting materials.

| Example | Name | MS (M + H)⁺ or (M + H)⁻ |
|---|---|---|
| 64 | 6-tert-Butyl-8-(3-morpholin-4-yl-propylamino)-5-m-tolyl-2H-[1,2,4]triazolo[4,3-a]pyrazin-3-one | 425.4 (+) |
| 65 | 6-Isopropyl-5-phenyl-8-(2-pyridin-3-yl-ethylamino)-2H-[1,2,4]triazolo[4,3-a]pyrazin-3-one | 373.3 (−) |
| 66 | 6-Isopropyl-8-(3-morpholin-4-yl-propylamino)-5-phenyl-2H-[1,2,4]triazolo[4,3-a]pyrazin-3-one | 397.4 (+) |
| 67 | 6-Isopropyl-5-methyl-8-(2-pyridin-3-yl-ethylamino)-2H-[1,2,4]triazolo[4,3-a]pyrazin-3-one | 313.3 (+) |
| 68 | 6-Isopropyl-5-methyl-8-(3-morpholin-4-yl-propylamino)-2H-[1,2,4]triazolo[4,3-a]pyrazin-3-one | 335.4 (+) |
| 69 | 6-tert-Butyl-5-phenyl-8-(2-pyridin-3-yl-ethylamino)-2H-[1,2,4]triazolo[4,3-a]pyrazin-3-one | 389.4 (+) |
| 70 | 6-tert-Butyl-8-(3-morpholin-4-yl-propylamino)-5-phenyl-2H-[1,2,4]triazolo[4,3-a]pyrazin-3-one | 411.4 (+) |
| 71 | 6-tert-Butyl-8-(2-hydroxy-propylamino)-2H-[1,2,4]triazolo[4,3-a]pyrazin-3-one | 435.5 (+) |

EXAMPLE 72

6-tert-Butyl-8-(3-dimethylamino-propylamino)-2H-[1,2,4]triazolo[4,3-a]pyrazin-3-one A solution of 23 mg of 6-tert-butyl-8-chloro-2H-[1,2,4]triazolo[4,3-a]pyrazin-3-one and 41 mg of 3-(dimethylamino)propylamine in DMF (0.5 mL) was heated to 80° C. After 16 h, the product was purified on a Shimadzu reverse-phase HPLC (Shimadzu LC-8A Preparatory LC; Waters Symmetry 30×50 mm column; solvent gradient=15-100% acetontrile/1% aqueous formic acid; flow rate=40 mL/min.) to provide the title compound as a white solid. MS (M+H$^+$)= 293.2.

The following examples were prepared in a manner analogous to that described in Example 72 using appropriate starting materials.

| Example | Name | MS (M + H$^+$) or (M + H$^-$) |
| --- | --- | --- |
| 73 | 6-tert-Butyl-8-(4-diethylamino-butylamino)-2H-[1,2,4]triazolo[4,3-a]pyrazin-3-one | 333.0 (−) |
| 74 | 6-tert-Butyl-8-[1-(R)-cyclohexyl-ethylamino]-2H-[1,2,4]triazolo[4,3-a]pyrazin-3-one | 316.2 (−) |
| 75 | 4-(6-tert-Butyl-3-oxo-2,3-dihydro-[1,2,4]triazolo[4,3-a]pyrazin-8-ylamino)-piperidine-1-carboxylic acid ethyl ester | 363.2 (+) |
| 76 | 6-tert-Butyl-8-(4-dimethylamino-butylamino)-2H-[1,2,4]triazolo[4,3-a]pyrazin-3-one | 307.3 (+) |
| 77 | 6-tert-Butyl-8-(3-piperidin-1-yl-propylamino)-2H-[1,2,4]triazolo[4,3-a]pyrazin-3-one | 332.2 (−) |

EXAMPLE 78

6-tert-Butyl-8-(piperidin-4-ylamino)-2H-[1,2,4]triazolo[4,3-a]pyrazin-3-one

A solution of 45 mg of 4-(6-tert-butyl-3-oxo-2,3-dihydro-[1,2,4]triazolo[4,3-a]pyrazin-8-ylamino)-piperidine-1-carboxylic acid ethyl ester in dioxane (10 mL) was treated with 6N KOH (1.0 mL) and the mixture was heated to reflux. After eight h, the reaction mixture was concentrated and the residue was dissolved in 48% HBr and heated at 80° C. After 14 h, the reaction mixture was concentrated to afford the title compound as a tan solid. MS (M+H$^+$)=290.3.

EXAMPLE 79

6-tert-Butyl-8-(2-p-tolyloxy-ethylamino)-2H-[1,2,4]triazolo[4,3-a]pyrazin-3-one

To a solution of 60 mg of 6-tert-butyl-8-chloro-2H-[1,2,4]triazolo[4,3-a]pyrazin-3-one and 100 mg of 2-p-tolyloxy-ethylamine hydrochloride in DMF (2.0 mL) was added 60 mg of TEA. The mixture was heated to 80° C. for three h and then was cooled to ambient temperature and partitioned between EtOAc and water. The organic layer was washed with sat. sodium chloride solution and then dried over sodium sulfate, filtered, and concentrated. The residue was purified by silica gel chromatography to afford the title compound as a white solid. MS (M+H$^+$)=342.5.

The following examples were prepared in a manner analogous to that described in Example 79 using appropriate starting materials.

| Example | Name | MS (M + H$^+$) or (M + H$^-$) |
| --- | --- | --- |
| 80 | 6-tert-Butyl-8-[2-(4-fluoro-phenoxy)-ethylamino]-2H-[1,2,4]triazolo[4,3-a]pyrazin-3-one | 346.6 (+) |
| 81 | 6-tert-Butyl-8-[2-(4-chloro-3-fluoro-phenoxy)-ethylamino]-2H-[1,2,4]triazolo[4,3-a]pyrazin-3-one | 378.4 (−) |
| 82 | 6-tert-Butyl-8-[2-(3,4-dichloro-phenoxy)-ethylamino]-2H-[1,2,4]triazolo[4,3-a]pyrazin-3-one | 396.3 (+) |
| 83 | 6-tert-Butyl-8-[2-(3-trifluoromethyl-phenoxy)-ethylamino]-2H-[1,2,4]triazolo[4,3-a]pyrazin-3-one | 396.4 (+) |
| 84 | 6-tert-Butyl-8-[2-(2-methyl-pyridin-3-yloxy)-ethylamino]-2H-[1,2,4]triazolo[4,3-a]pyrazin-3-one | 343.4 (+) |
| 85 | 3-[2-(6-tert-Butyl-3-oxo-2,3-dihydro-[1,2,4]triazolo[4,3-a]pyrazin-8-ylamino)-ethoxy]-benzonitrile | 353.4 (+) |
| 86 | 8-[2-(4-Bromo-phenoxy)-ethylamino]-6-tert-butyl-2H-[1,2,4]triazolo[4,3-a]pyrazin-3-one | 406.4 (−) |
| 87 | 6-tert-Butyl-8-[2-(4-chloro-phenoxy)-ethylamino]-2H-[1,2,4]triazolo[4,3-a]pyrazin-3-one | 360.4 (−) |
| 88 | 6-tert-Butyl-8-[2-(6-methyl-pyridin-3-yloxy)-ethylamino]-2H-[1,2,4]triazolo[4,3-a]pyrazin-3-one | 343.5 (+) |
| 89 | 6-tert-Butyl-8-[2-(pyrazin-2-yloxy)-ethylamino]-2H-[1,2,4]triazolo[4,3-a]pyrazin-3-one | 330.5 (+) |
| 90 | 6-tert-Butyl-8-[2-(6-methoxy-pyridazin-3-yloxy)-ethylamino]-2H-[1,2,4]triazolo[4,3-a]pyrazin-3-one | 360.4 (+) |
| 91 | 8-[2-(3-Amino-pyridin-2-yloxy)-ethylamino]-6-tert-butyl-2H-[1,2,4]triazolo[4,3-a]pyrazin-3-one | 344.4 (+) |
| 92 | 6-tert-Butyl-8-[2-(4-chloro-2-methyl-phenoxy)-ethylamino]-2H-[1,2,4]triazolo[4,3-a]pyrazin-3-one | 376.4 (+) |
| 93 | 6-tert-Butyl-8-(2-o-tolyloxy-ethylamino)-2H-[1,2,4]triazolo[4,3-a]pyrazin-3-one | 342.4 (+) |
| 94 | 6-tert-Butyl-8-[2-(pyridin-3-yloxy)-ethylamino]-2H-[1,2,4]triazolo[4,3-a]pyrazin-3-one | 329.4 (+) |
| 95 | 6-tert-Butyl-8-[2-(pyridin-4-yloxy)-ethylamino]-2H-[1,2,4]triazolo[4,3-a]pyrazin-3-one | 327.4 (−) |
| 96 | 5-[2-(6-tert-Butyl-3-oxo-2,3-dihydro-[1,2,4]triazolo[4,3-a]pyrazin-8-ylamino)-ethoxy]-nicotinic acid methyl ester | 387.5 (+) |
| 97 | 6-tert-Butyl-8-[2-(6-methoxy-pyridin-3-yloxy)-ethylamino]-2H-[1,2,4]triazolo[4,3-a]pyrazin-3-one | 359.4 (+) |

EXAMPLE 98

8-(2-Amino-ethylamino)-6-tert-butyl-2H-[1,2,4]triazolo[4,3-a]pyrazin-3-one

A solution of 100 mg of [2-(6-tert-butyl-3-oxo-2,3-dihydro-[1,2,4]triazolo[4,3-a]pyrazin-8-ylamino)-ethyl]-carbamic acid tert-butyl ester in dichloromethane (5.0 mL) was treated with 1.48 g of TFA at ambient temperature for 16 h. The solvent was removed and the residue was recrystallized from ether to afford the title compound as a white solid. MS (M+H$^+$)=251.3.

EXAMPLE 99

N-[2-(6-tert-Butyl-3-oxo-2,3-dihydro-[1,2,4]triazolo[4,3-a]pyrazin-8-ylamino)-ethyl]-benzenesulfonamide A solution of 50 mg of 8-(2-amino-ethylamino)-6-tert-butyl-2H-[1,2,4]triazolo[4,3-a]pyrazin-3-one, 97 mg of phenylsulfonyl chloride and 61 mg of diisopropylethylamine in DMF (1.0 mL) was stirred at ambient temperature for 16 h. The reaction mixture was diluted with EtOAc and washed with water and then sat. sodium chloride solution. The organic layer was dried over sodium sulfate, filtered, and concentrated. The residue was purified by silica gel chromatography to provide the title compound as a white solid. MS (M+H$^+$)=391.4.

EXAMPLES 100 AND 101

6-tert-Butyl-8-(2-ethanesulfonyl-ethylamino)-2H-[1,2,4]triazolo[4,3-a]pyrazin-3-one and 6-tert-Butyl-8-(2-ethanesulfinyl-ethylamino)-2H-[1,2,4]triazolo[4,3-a]pyrazin-3-one To a solution of 113 mg of 6-tert-butyl-8-(2-ethylsulfanyl-ethylamino)-2H-[1,2,4]triazolo[4,3-a]pyrazin-3-one in AcOH (1.0 mL) was added 32% peracetic acid (0.8 mL) and the mixture was stirred at ambient temperature. After 16 h, the reaction as diluted with water and extracted with EtOAc and the organic extract was washed with sat. sodium chloride solution, dried over magnesium sulfate, filtered, and concentrated. The residue was purified by silica gel chromatography to provide the title compounds as white solids. 6-tert-Butyl-8-(2-ethanesulfonyl-ethylamino)-2H-[1,2,4]triazolo[4,3-a]pyrazin-3-one: MS (M+H$^+$)=328.3; 6-tert-Butyl-8-(2-ethanesulfinyl-ethylamino)-2H-[1,2,4]triazolo[4,3-a]pyrazin-3-one: MS (M+H$^+$)=310.6.

EXAMPLE 102

6-tert-Butyl-5-(1-hydroxy-3-methyl-butyl)-8-(2-pyridin-3-yl-ethylamino)-2H-[1,2,4]triazolo[4,3-a]pyrazin-3-one Step A A flame-dried flask was charged with THF (3.0 mL) and 423 mg of 2,2,6,6-tetramethylpiperidine. The solution was cooled to −30° C. and 1.0 mL of a 2.5 M solution of n-butyl-lithium in hexanes was added dropwise. The mixture was warmed to 0° C. for 20 min. and then cooled to −78° C. A solution of 226 mg of 6-tert-butyl-8-chloro-2H-[1,2,4]triazolo[4,3-a]pyrazin-3-one in THF (2.0 mL) was added dropwise and the resulting solution was stirred for one h prior to the addition of 129 mg of isobutyraldehyde. The mixture was warmed to 0° C. and the reaction was quenched by the addition of sat. ammonium chloride solution followed by adjusting the pH of the solution to 3.0 with 2N HCl. The mixture was extracted with EtOAc and the organic layer was washed with sat. sodium chloride solution, dried over sodium sulfate, filtered, and concentrated. The residue was purified by silica gel chromatography to provide 6-tert-butyl-8-chloro-5-(1-hydroxy-3-methyl-butyl)-2H-[1,2,4]triazolo[4,3-a]pyrazin-3-one as a white solid. MS (M+H$^+$)=313.4.

Step B

A solution of 70 mg of the product of Step A, 34 mg of TEA and 33 mg of 2-pyridin-3-yl-ethylamine in 1-methyl-2-pyrrolidinone (1.5 mL) was heated to 80° C. After six h, the reaction mixture was cooled, poured into water and extracted with EtOAc and then 15% IPA/chloroform. The organic extracts were washed dried over sodium sulfate, filtered, and concentrated. The residue was dissolved in EtOAc and washed with water and sat. sodium chloride solution. The organic layer was dried over sodium sulfate, filtered, concentrated, and the residue was recrystallized from ether/hexanes to provide the title compound as a white solid. MS (M+H$^+$)=397.4.

The following examples were prepared in a manner analogous to that described in Example 102 using appropriate starting materials

| Example | Name | MS (M + H$^+$) or (M + H$^-$) |
|---|---|---|
| 103 | 6-tert-Butyl-5-(1-hydroxy-2-methyl-propyl)-8-(2-pyridin-3-yl-ethylamino)-2H-[1,2,4]triazolo[4,3-a]pyrazin-3-one | 383.4 (+) |
| 104 | 6-tert-Butyl-5-(1-hydroxy-3-phenyl-propyl)-8-(2-pyridin-3-yl-ethylamino)-2H-[1,2,4]triazolo[4,3-a]pyrazin-3-one | 445.4 (−) |
| 105 | 5-(1-Hydroxy-3-methyl-butyl)-6-isopropyl-8-isopropylamino-2H-[1,2,4]triazolo[4,3-a]pyrazin-3-one | 320.4 (−) |
| 106 | 5-(1-Hydroxy-3-methyl-butyl)-6-isopropyl-8-(2-pyridin-3-yl-ethylamino)-2H-[1,2,4]triazolo[4,3-a]pyrazin-3-one | 383.4 (−) |
| 107 | 6-tert-Butyl-5-(1-hydroxy-3-phenyl-propyl)-8-isopropylamino-2H-[1,2,4]triazolo[4,3-a]pyrazin-3-one | 383.4 (−) |
| 108 | 6-tert-Butyl-5-(1-hydroxy-3-pyridin-3-yl-propyl)-8-(2-pyridin-3-yl-ethylamino)-2H-[1,2,4]triazolo[4,3-a]pyrazin-3-one | 446.5 (−) |
| 109 | 5-(1-Hydroxy-3-phenyl-propyl)-6-isopropyl-8-isopropylamino-2H-[1,2,4]triazolo[4,3-a]pyrazin-3-one | 370.4 (+) |
| 110 | 5-(1-Hydroxy-3-phenyl-propyl)-6-isopropyl-8-(2-pyridin-3-yl-ethylamino)-2H-[1,2,4]triazolo[4,3-a]pyrazin-3-one | 431.4 (−) |
| 111 | 5-(1-Hydroxy-2-phenyl-ethyl)-6-isopropyl-8-(2-pyridin-3-yl-ethylamino)-2H-[1,2,4]triazolo[4,3-a]pyrazin-3-one | 417.4 (−) |
| 112 | 6-tert-Butyl-5-[1-hydroxy-3-(4-trifluoromethyl-phenyl)-propyl]-8-(2-pyridin-3-yl-ethylamino)-2H-[1,2,4]triazolo[4,3-a]pyrazin-3-one | 513.3 (−) |
| 113 | 6-tert-Butyl-5-[3-(4-fluoro-phenyl)-1-hydroxy-propyl]-8-(2-pyridin-3-yl-ethylamino)-2H-[1,2,4]triazolo[4,3-a]pyrazin-3-one | 463.3 (−) |
| 114 | 6-tert-Butyl-5-(1-hydroxy-4-phenyl-butyl)-8-(2-pyridin-3-yl-ethylamino)-2H-[1,2,4]triazolo[4,3-a]pyrazin-3-one | 461.4 (+) |
| 115 | 6-tert-Butyl-5-[3-(4-chloro-phenyl)-1-hydroxy-propyl]-8-(2-pyridin-3-yl-ethylamino)-2H-[1,2,4]triazolo[4,3-a]pyrazin-3-one | 479.3 (−) |
| 116 | 1-(S)-6-tert-Butyl-5-(1-hydroxy-3-phenyl-propyl)-8-(2-pyridin-3-yl-ethylamino)-2H-[1,2,4]triazolo[4,3-a]pyrazin-3-one | 479.3 (−) |
| 117 | 1-(R)-6-tert-Butyl-5-(1-hydroxy-3-phenyl-propyl)-8-(2-pyridin-3-yl-ethylamino)-2H-[1,2,4]triazolo[4,3-a]pyrazin-3-one | 479.3 (−) |

EXAMPLE 118

6-Isopropyl-8-isopropylamino-5-(3-methyl-but-1-enyl)-2H-[1,2,4]triazolo[4,3-a]pyrazin-3-one To concentrated sulfuric acid (0.2 mL) at 0° C. was added 64 mg of 6-tert-butyl-5-(1-hydroxy-3-methyl-butyl)-8-(2-pyridin-3-yl-ethylamino)-2H-[1,2,4]triazolo[4,3-a]pyrazin- 3-one. After five min., the reaction was quenched by the addition of ice (2 mL) and the pH was adjusted to 4 with 2N NaOH solution. The resulting precipitate was collected and washed with water and air-dried to provide the title compound. MS (M+H$^+$)=302.4.

EXAMPLE 119

6-Isopropyl-8-isopropylamino-5-(3-methyl-butyl)-2H-[1,2,4]triazolo[4,3-a]pyrazin-3-one A solution of 30 mg of 6-isopropyl-8-isopropylamino-5-(3-methyl-but-1-enyl)-2H-[1,2,4]triazolo[4,3-a]pyrazin-3-one in EtOH (10 mL) was treated with 50 mg of 10% Pd/C. The mixture was hydrogenated at 35 psi for one h and the solids were removed by filtration through diatomaceous earth. The filtrate was concentrated to provide the title compound as a white solid. MS (M+H$^+$)=304.4.

A high-speed preparative protocol for the synthesis of certain 8-amino-6-tert-butyl-2H-[1,2,4]triazolo[4,3-a]pyrazin-3-one analogs is exemplified in Example 120 hereinbelow.

EXAMPLE 120

6-tert-Butyl-8-[(pyridin-3-ylmethyl)-amino]-2H-[1,2,4]triazolo[4,3-a]pyrazin-3-one A solution of 43.2 mg of pyridin-3-ylmethylamine and 22.6 mg of 6-tert-butyl-8-chloro-2H-[1,2,4]triazolo[4,3-a]pyrazin-3-one in 1-methyl-2-pyrrolidinone (0.5 mL) was prepared in a 2 dram sealed vial. The reaction was shaken at 80° C. for 15 h, cooled to ambient temperature and purified by direct injection onto a reverse phase HPLC column (Shimadzu LC-8A Preparatory LC; Waters Symmetry 30×50 mm column; solvent gradient=15-100% acetontrile/1% aqueous formic acid; flow rate=40 mL/min.). Evaporation of the desired fractions afforded the title compound as a solid. MS (M+H$^+$)=297.6.

The following examples were prepared in a manner analogous to that described in Example 120 using appropriate starting materials. If the amine reactant was employed in the form of an acid addition salt, then TEA was also included in the reaction mixture.

| Example | Name | MS (M + H$^+$) or (M + H$^-$) |
|---|---|---|
| 121 | 6-tert-Butyl-8-(3-morpholin-4-yl-propylamino)-2H-[1,2,4]triazolo[4,3-a]pyrazin-3-one | 335.4 (+) |
| 122 | 6-tert-Butyl-8-(2-pyridin-2-yl-ethylamino)-2H-[1,2,4]triazolo[4,3-a]pyrazin-3-one | 313.3 (+) |
| 123 | 6-tert-Butyl-8-(2-pyridin-4-yl-ethylamino)-2H-[1,2,4]triazolo[4,3-a]pyrazin-3-one | 313.4 (+) |
| 124 | 4-(6-tert-Butyl-3-oxo-2,3-dihydro-[1,2,4]triazolo[4,3-a]pyrazin-8-ylamino)-butyric acid | 292.2 (−) |
| 125 | 5-(6-tert-Butyl-3-oxo-2,3-dihydro-[1,2,4]triazolo[4,3-a]pyrazin-8-ylamino)-pentanoic acid | 306.2 (−) |
| 126 | 6-tert-Butyl-8-[2-(1H-indol-3-yl)-ethylamino]-2H-[1,2,4]triazolo[4,3-a]pyrazin-3-one | 349.7 (−) |
| 127 | 6-(6-tert-Butyl-3-oxo-2,3-dihydro-[1,2,4]triazolo[4,3-a]pyrazin-8-ylamino)-hexanoic acid | 320.7 (−) |
| 128 | 6-tert-Butyl-8-[2-(4-hydroxy-phenyl)-ethylamino]-2H-[1,2,4]triazolo[4,3-a]pyrazin-3-one | 326.7 (−) |
| 129 | 6-tert-Butyl-8-[2-(3,4-dihydroxy-phenyl)-2-hydroxy-ethylamino]-2H-[1,2,4]triazolo[4,3-a]pyrazin-3-one | 358.2 (−) |
| 130 | 6-tert-Butyl-8-[2-(1H-imidazol-4-yl)-ethylamino]-2H-[1,2,4]triazolo[4,3-a]pyrazin-3-one | 300.6 (−) |
| 131 | 6-tert-Butyl-8-(3-phenyl-propylamino)-2H-[1,2,4]triazolo[4,3-a]pyrazin-3-one | 324.7 (−) |
| 132 | 6-tert-Butyl-8-[2-(4-chloro-phenyl)-ethylamino]-2H-[1,2,4]triazolo[4,3-a]pyrazin-3-one | 344.6 (−) |
| 133 | 4-[(6-tert-Butyl-3-oxo-2,3-dihydro-[1,2,4]triazolo[4,3-a]pyrazin-8-ylamino)-methyl]-benzoic acid | 340.7 (−) |
| 134 | 8-[(Benzo[1,3]dioxol-5-ylmethyl)-amino]-6-tert-butyl-2H-[1,2,4]triazolo[4,3-a]pyrazin-3-one | 340.7 (−) |
| 135 | 6-tert-Butyl-8-[2-(4-fluoro-phenyl)-ethylamino]-2H-[1,2,4]triazolo[4,3-a]pyrazin-3-one | 328.7 (−) |
| 136 | 6-tert-Butyl-8-(2-mercapto-ethylamino)-2H-[1,2,4]triazolo[4,3-a]pyrazin-3-one | 533.0 (+) |
| 137 | 6-tert-Butyl-8-[(pyridin-4-ylmethyl)-amino]-2H-[1,2,4]triazolo[4,3-a]pyrazin-3-one | 297.6 (−) |
| 138 | 6-tert-Butyl-8-[2-(3-methoxy-phenyl)-ethylamino]-2H-[1,2,4]triazolo[4,3-a]pyrazin-3-one | 340.7 (−) |
| 139 | 6-tert-Butyl-8-(2-ethylsulfanyl-ethylamino)-2H-[1,2,4]triazolo[4,3-a]pyrazin-3-one | 294.6 (−) |
| 140 | 6-tert-Butyl-8-(3,3-diphenyl-propylamino)-2H-[1,2,4]triazolo[4,3-a]pyrazin-3-one | 401.8 (−) |
| 141 | 6-tert-Butyl-8-(4-nitro-benzylamino)-2H-[1,2,4]triazolo[4,3-a]pyrazin-3-one | 341.7 (−) |
| 142 | 8-[2-(4-Bromo-phenyl)-2-oxo-ethylamino]-6-tert-butyl-2H-[1,2,4]triazolo[4,3-a]pyrazin-3-one | 403.8 (−) |
| 143 | 4-[(6-tert-Butyl-3-oxo-2,3-dihydro-[1,2,4]triazolo[4,3-a]pyrazin-8-ylamino)-methyl]-benzenesulfonamide | 376.6 (−) |

-continued

| Example | Name | MS (M + H+) or (M + H−) |
|---|---|---|
| 144 | 6-tert-Butyl-8-(2-hydroxy-1-methyl-ethylamino)-2H-[1,2,4]triazolo[4,3-a]pyrazin-3-one | 264.6 (−) |
| 145 | 6-tert-Butyl-8-(6-hydroxy-hexylamino)-2H-[1,2,4]triazolo[4,3-a]pyrazin-3-one | 306.7 (−) |
| 146 | 8-[2-(5-Benzyloxy-1H-indol-3-yl)-ethylamino]-6-tert-butyl-2H-[1,2,4]triazolo[4,3-a]pyrazin-3-one | 455.9 (−) |
| 147 | 2R-6-tert-Butyl-8-[(6,6-dimethyl-bicyclo[3.1.1]hept-2-ylmethyl)-amino]-2H-[1,2,4]triazolo[4,3-a]pyrazin-3-one | 344.8 (+) |
| 148 | 6-tert-Butyl-8-(2-hydroxy-1-methyl-2-phenyl-ethylamino)-2H-[1,2,4]triazolo[4,3-a]pyrazin-3-one | 340.7 (−) |
| 149 | 6-tert-Butyl-8-(2-methoxy-ethylamino)-2H-[1,2,4]triazolo[4,3-a]pyrazin-3-one | 264.5 (−) |
| 150 | 8-(2-Benzylsulfanyl-ethylamino)-6-tert-butyl-2H-[1,2,4]triazolo[4,3-a]pyrazin-3-one | 356.7 (−) |
| 151 | 4-(6-tert-Butyl-3-oxo-2,3-dihydro-[1,2,4]triazolo[4,3-a]pyrazin-8-ylamino)-3-hydroxy-butyric acid | 308.6 (−) |
| 152 | 6-tert-Butyl-8-[2-(4-methoxy-phenyl)-ethylamino]-2H-[1,2,4]triazolo[4,3-a]pyrazin-3-one | 340.7 (−) |
| 153 | 6-tert-Butyl-8-(2-imidazo[1,2-a]pyridin-2-yl-ethylamino)-2H-[1,2,4]triazolo[4,3-a]pyrazin-3-one | 350.3 (−) |
| 154 | 2S-1-[(6-tert-Butyl-3-oxo-2,3-dihydro-[1,2,4]triazolo[4,3-a]pyrazin-8-ylamino)-acetyl]-pyrrolidine-2-carboxylic acid | 363.5 (−) |
| 155 | 4-[(6-tert-Butyl-3-oxo-2,3-dihydro-[1,2,4]triazolo[4,3-a]pyrazin-8-ylamino)-methyl]-cyclohexane carboxylic acid | 348.6 (−) |
| 156 | 6-tert-Butyl-8-(3,4-dihydroxy-benzylamino)-2H-[1,2,4]triazolo[4,3-a]pyrazin-3-one | 330.5 (−) |
| 157 | 6-tert-Butyl-8-[(3-hydroxy-5-hydroxymethyl-2-methyl-pyridin-4-ylmethyl)-amino]-2H-[1,2,4]triazolo[4,3-a]pyrazin-3-one | 359.6 (−) |
| 158 | 6-tert-Butyl-8-[2-(4-phenoxy-phenyl)-ethylamino]-2H-[1,2,4]triazolo[4,3-a]pyrazin-3-one | 404.6 (−) |
| 159 | 8-[2-(3-Bromo-4-methoxy-phenyl)-ethylamino]-6-tert-butyl-2H-[1,2,4]triazolo[4,3-a]pyrazin-3-one | 421.5 (−) |
| 160 | 6-tert-Butyl-8-[2-(2-chloro-6-fluoro-benzylsulfanyl)-ethylamino]-2H-[1,2,4]triazolo[4,3-a]pyrazin-3-one | 408.6 (−) |
| 161 | 6-tert-Butyl-8-[2-(5-dimethylaminomethyl-furan-2-ylmethylsulfanyl)-ethylamino]-2H-[1,2,4]triazolo[4,3-a]pyrazin-3-one | 405.7 (−) |
| 162 | 6-tert-Butyl-8-(3-methylsulfanyl-propylamino)-2H-[1,2,4]triazolo[4,3-a]pyrazin-3-one | 296.5 (−) |
| 163 | 6-tert-Butyl-8-(4-phenyl-butylamino)-2H-[1,2,4]triazolo[4,3-a]pyrazin-3-one | 340.6 (−) |
| 164 | 6-tert-Butyl-8-[2-(3,4-dimethoxy-phenyl)-ethylamino]-2H-[1,2,4]triazolo[4,3-a]pyrazin-3-one | 372.6 (−) |
| 165 | 6-tert-Butyl-8-(1-phenyl-ethylamino)-2H-[1,2,4]triazolo[4,3-a]pyrazin-3-one | 312.6 (−) |
| 166 | 6-tert-Butyl-8-(2-oxo-2-phenyl-ethylamino)-2H-[1,2,4]triazolo[4,3-a]pyrazin-3-one | 326.6 (−) |
| 167 | 6-tert-Butyl-8-(2-ethoxy-benzylamino)-2H-[1,2,4]triazolo[4,3-a]pyrazin-3-one | 342.6 (−) |
| 168 | 6-tert-Butyl-8-(2-cyclohex-1-enyl-ethylamino)-2H-[1,2,4]triazolo[4,3-a]pyrazin-3-one | 316.6 (−) |
| 169 | 6-tert-Butyl-8-(3,4-dichloro-benzylamino)-2H-[1,2,4]triazolo[4,3-a]pyrazin-3-one | 367.4 (−) |
| 170 | 6-tert-Butyl-8-[(furan-2-ylmethyl)-amino]-2H-[1,2,4]triazolo[4,3-a]pyrazin-3-one | 288.2 (−) |
| 171 | 6-tert-Butyl-8-(2-dimethylamino-ethylamino)-2H-[1,2,4]triazolo[4,3-a]pyrazin-3-one | 279.6 (−) |
| 172 | 6-tert-Butyl-8-(2,2-diphenyl-ethylamino)-2H-[1,2,4]triazolo[4,3-a]pyrazin-3-one | 389.1 (−) |
| 173 | 6-tert-Butyl-8-[2-(2,3-dimethoxy-phenyl)-ethylamino]-2H-[1,2,4]triazolo[4,3-a]pyrazin-3-one | 372.2 (−) |
| 174 | 6-tert-Butyl-8-[2-(2-ethoxy-phenyl)-ethylamino]-2H-[1,2,4]triazolo[4,3-a]pyrazin-3-one | 356.6 (−) |
| 175 | N-[2-(6-tert-Butyl-3-oxo-2,3-dihydro-[1,2,4]triazolo[4,3-a]pyrazin-8-ylamino)-ethyl]-acetamide | 291.3 (−) |
| 176 | [2-(6-tert-Butyl-3-oxo-2,3-dihydro-[1,2,4]triazolo[4,3-a]pyrazin-8-ylamino)-ethyl]-carbamic acid tert-butyl ester | 351.4 (+) |
| 177 | 6-tert-Butyl-8-[(tetrahydro-furan-2-ylmethyl)-amino]-2H-[1,2,4]triazolo[4,3-a]pyrazin-3-one | 292.4 (+) |

-continued

| Example | Name | MS (M + H+) or (M + H−) |
|---|---|---|
| 178 | 6-tert-Butyl-8-[2-(2-hydroxy-ethoxy)-ethylamino]-2H-[1,2,4]triazolo[4,3-a]pyrazin-3-one | 296.4 (+) |
| 179 | 6-tert-Butyl-8-[(2,2-dimethyl-[1,3]dioxolan-4-ylmethyl)-amino]-2H-[1,2,4]triazolo[4,3-a]pyrazin-3-one | 322.4 (+) |
| 180 | 6-tert-Butyl-8-(2,2-dimethoxy-ethylamino)-2H-[1,2,4]triazolo[4,3-a]pyrazin-3-one | 296.4 (+) |
| 181 | 6-tert-Butyl-8-(4-methoxy-benzylamino)-2H-[1,2,4]triazolo[4,3-a]pyrazin-3-one | 326.6 (−) |
| 182 | 6-tert-Butyl-8-(2-hydroxy-propylamino)-2H-[1,2,4]triazolo[4,3-a]pyrazin-3-one | 264.4 (−) |
| 183 | 5-(6-tert-Butyl-3-oxo-2,3-dihydro-[1,2,4]triazolo[4,3-a]pyrazin-8-ylamino)-4-oxo-pentanoic acid | 320.4 (−) |
| 184 | 8-[(1H-Benzoimidazol-2-ylmethyl)-amino]-6-tert-butyl-2H-[1,2,4]triazolo[4,3-a]pyrazin-3-one | 336.8 (−) |
| 185 | 4-[(6-tert-Butyl-3-oxo-2,3-dihydro-[1,2,4]triazolo[4,3-a]pyrazin-8-ylamino)-methyl]-cyclohexanecarbonitrile | 327.8 (−) |
| 186 | 8-[(3-Aminomethyl-cyclohexylmethyl)-amino]-6-tert-butyl-2H-[1,2,4]triazolo[4,3-a]pyrazin-3-one | 331.8 (−) |
| 187 | 6-tert-Butyl-8-[(6,6-dimethyl-bicyclo[3.1.1]hept-2-ylmethyl)-amino]-2H-[1,2,4]triazolo[4,3-a]pyrazin-3-one | 342.8 (−) |
| 188 | 6-tert-Butyl-8-{3-[4-(4-chloro-phenyl)-3,6-dihydro-2H-pyridin-1-yl]-propylamino}-2H-[1,2,4]triazolo[4,3-a]pyrazin-3-one | 339.9 (−) |
| 189 | 6-tert-Butyl-8-[(naphthalen-1-ylmethyl)-amino]-2H-[1,2,4]triazolo[4,3-a]pyrazin-3-one | 346.7 (−) |
| 190 | 6-tert-Butyl-8-[(6-methyl-pyridin-3-ylmethyl)-amino]-2H-[1,2,4]triazolo[4,3-a]pyrazin-3-one | 311.8 (−) |
| 191 | 6-tert-Butyl-8-[1-(5-methyl-1H-benzoimidazol-2-yl)-ethylamino]-2H-[1,2,4]triazolo[4,3-a]pyrazin-3-one | 364.8 (−) |
| 192 | 6-tert-Butyl-8-[(1-methyl-pyrrolidin-3-ylmethyl)-amino]-2H-[1,2,4]triazolo[4,3-a]pyrazin-3-one | 303.8 (−) |
| 193 | 6-tert-Butyl-8-[(1-o-tolyl-1H-pyrazol-4-ylmethyl)-amino]-2H-[1,2,4]triazolo[4,3-a]pyrazin-3-one | 376.8 (−) |
| 194 | 6-tert-Butyl-8-[(isochroman-1-ylmethyl)-amino]-2H-[1,2,4]triazolo[4,3-a]pyrazin-3-one | 352.8 (−) |
| 195 | 6-tert-Butyl-8-[(1-methyl-piperidin-2-ylmethyl)-amino]-2H-[1,2,4]triazolo[4,3-a]pyrazin-3-one | 317.7 (−) |
| 196 | 6-tert-Butyl-8-(2-methyl-2-morpholin-4-yl-propylamino)-2H-[1,2,4]triazolo[4,3-a]pyrazin-3-one | 349.8 (+) |
| 197 | 6-tert-Butyl-8-[1-(1,3,5-trimethyl-1H-pyrazol-4-yl)-ethylamino]-2H-[1,2,4]triazolo[4,3-a]pyrazin-3-one | 344.8 (+) |
| 198 | 6-tert-Butyl-8-[(4-phenyl-thiazol-2-ylmethyl)-amino]-2H-[1,2,4]triazolo[4,3-a]pyrazin-3-one | 379.7 (−) |
| 199 | 6-tert-Butyl-8-(1-methyl-2-morpholin-4-yl-ethylamino)-2H-[1,2,4]triazolo[4,3-a]pyrazin-3-one | 333.7 (−) |
| 200 | 6-tert-Butyl-8-(3-vinyloxy-propylamino)-2H-[1,2,4]triazolo[4,3-a]pyrazin-3-one | 290.6 (−) |
| 201 | 6-tert-Butyl-8-[(1-methyl-piperidin-3-ylmethyl)-amino]-2H-[1,2,4]triazolo[4,3-a]pyrazin-3-one | 317.7 (−) |
| 202 | 8-[(1-Benzyl-pyrrolidin-3-ylmethyl)-amino]-6-tert-butyl-2H-[1,2,4]triazolo[4,3-a]pyrazin-3-one | 379.8 (−) |
| 203 | 6-tert-Butyl-8-(2-furan-2-yl-ethylamino)-2H-[1,2,4]triazolo[4,3-a]pyrazin-3-one | 300.6 (−) |
| 204 | 6-tert-Butyl-8-[(1-methyl-1,2,3,4-tetrahydro-quinolin-6-ylmethyl)-amino]-2H-[1,2,4]triazolo[4,3-a]pyrazin-3-one | 365.8 (−) |
| 205 | 6-tert-Butyl-8-[(1-methyl-1H-pyrazol-4-ylmethyl)-amino]-2H-[1,2,4]triazolo[4,3-a]pyrazin-3-one | 300.6 (−) |
| 206 | 6-tert-Butyl-8-[(1-morpholin-4-yl-cyclohexylmethyl)-amino]-2H-[1,2,4]triazolo[4,3-a]pyrazin-3-one | 387.8 (−) |
| 207 | 6-tert-Butyl-8-[(1-piperidin-1-yl-cyclohexylmethyl)-amino]-2H-[1,2,4]triazolo[4,3-a]pyrazin-3-one | 385.8 (−) |
| 208 | 6-tert-Butyl-8-(1-methyl-2-pyrrolidin-1-yl-ethylamino)-2H-[1,2,4]triazolo[4,3-a]pyrazin-3-one | 317.7 (−) |
| 209 | 6-tert-Butyl-8-[(thiophen-2-ylmethyl)-amino]-2H-[1,2,4]triazolo[4,3-a]pyrazin-3-one | 302.7 (−) |
| 210 | 6-tert-Butyl-8-(2-thiophen-2-yl-ethylamino)-2H-[1,2,4]triazolo[4,3-a]pyrazin-3-one | 316.7 (−) |
| 211 | 6-tert-Butyl-8-[1-(4-hydroxy-phenyl)-ethylamino]-2H-[1,2,4]triazolo[4,3-a]pyrazin-3-one | 326.6 (−) |
| 212 | 6-tert-Butyl-8-[3-(2-methyl-piperidin-1-yl)-propylamino]-2H-[1,2,4]triazolo[4,3-a]pyrazin-3-one | 345.7 (−) |
| 213 | 6-tert-Butyl-8-(3,4,5-trimethoxy-benzylamino)-2H-[1,2,4]triazolo[4,3-a]pyrazin-3-one | 386.7 (−) |

-continued

| Example | Name | MS (M + H⁺) or (M + H⁻) |
|---|---|---|
| 214 | 6-tert-Butyl-8-[1-(4-fluoro-phenyl)-ethylamino]-2H-[1,2,4]triazolo[4,3-a]pyrazin-3-one | 328.6 (−) |
| 215 | 6-tert-Butyl-8-(2-phenoxy-ethylamino)-2H-[1,2,4]triazolo[4,3-a]pyrazin-3-one | 327.6 (−) |
| 216 | 6-tert-Butyl-8-[3-(4-methoxy-phenyl)-1-methyl-propylamino]-2H-[1,2,4]triazolo[4,3-a]pyrazin-3-one | 368.7 (−) |
| 217 | 2-[(6-tert-Butyl-3-oxo-2,3-dihydro-[1,2,4]triazolo[4,3-a]pyrazin-8-ylamino)-methyl]-piperidine-1-carboxylic acid tert-butyl ester | 403.8 (−) |
| 218 | 6-tert-Butyl-8-[2-(4-methoxy-phenoxy)-ethylamino]-2H-[1,2,4]triazolo[4,3-a]pyrazin-3-one | 356.7 (−) |
| 219 | 3-(6-tert-Butyl-3-oxo-2,3-dihydro-[1,2,4]triazolo[4,3-a]pyrazin-8-ylamino)-propionitrile | 261.3 (+) |
| 220 | 6-tert-Butyl-8-(3,3-dimethoxy-propylamino)-2H-[1,2,4]triazolo[4,3-a]pyrazin-3-one | 308.4 (+) |
| 221 | 6-tert-Butyl-8-(2-ethanesulfonyl-ethylamino)-2H-[1,2,4]triazolo[4,3-a]pyrazin-3-one | 294.4 (+) |
| 222 | 6-tert-Butyl-8-(3-methoxy-propylamino)-2H-[1,2,4]triazolo[4,3-a]pyrazin-3-one | 278.3 (−) |
| 223 | 6-tert-Butyl-8-[3-(2-oxo-pyrrolidin-1-yl)-propylamino]-2H-[1,2,4]triazolo[4,3-a]pyrazin-3-one | 331.3 (−) |
| 224 | 6-tert-Butyl-8-(3-imidazol-1-yl-propylamino)-2H-[1,2,4]triazolo[4,3-a]pyrazin-3-one | 314.5 (−) |
| 225 | [3-(6-tert-Butyl-3-oxo-2,3-dihydro-[1,2,4]triazolo[4,3-a]pyrazin-8-ylamino)-propyl]-methyl-carbamic acid tert-butyl ester | 377.4 (−) |
| 226 | 6-tert-Butyl-8-[2-(4-methyl-1H-imidazol-2-yl)-ethylamino]-2H-[1,2,4]triazolo[4,3-a]pyrazin-3-one | 314.3 (−) |
| 227 | 6-tert-Butyl-8-[2-(5-pyridin-4-yl-2H-[1,2,4]triazol-3-yl)-ethylamino]-2H-[1,2,4]triazolo[4,3-a]pyrazin-3-one | 378.4 (−) |
| 228 | 6-tert-Butyl-8-[2-(6-methoxy-1H-benzoimidazol-2-yl)-ethylamino]-2H-[1,2,4]triazolo[4,3-a]pyrazin-3-one | 380.4 (−) |
| 229 | 6-tert-Butyl-8-[2-(7-methyl-1H-benzoimidazol-2-yl)-ethylamino]-2H-[1,2,4]triazolo[4,3-a]pyrazin-3-one | 331.3 (−) |
| 230 | 6-tert-Butyl-8-[2-(1-methyl-1H-pyrazol-4-yl)-ethylamino]-2H-[1,2,4]triazolo[4,3-a]pyrazin-3-one | 314.3 (−) |
| 231 | 6-tert-Butyl-8-[2-(2-methyl-1H-indol-3-yl)-ethylamino]-2H-[1,2,4]triazolo[4,3-a]pyrazin-3-one | 363.4 (−) |
| 232 | 6-tert-Butyl-8-[2-(5-chloro-1H-benzoimidazol-2-yl)-ethylamino]-2H-[1,2,4]triazolo[4,3-a]pyrazin-3-one | 384.4 (−) |
| 233 | 6-tert-Butyl-8-[2-(3,5-dimethyl-1H-pyrazol-4-yl)-ethylamino]-2H-[1,2,4]triazolo[4,3-a]pyrazin-3-one | 328.4 (−) |
| 234 | 6-tert-Butyl-8-[3-(3,5-dimethyl-pyrazol-1-yl)-propylamino]-2H-[1,2,4]triazolo[4,3-a]pyrazin-3-one | 342.4 (−) |

EXAMPLE 235

6-tert-Butyl-8-[2-(6-methoxy-pyridin-3-yl)-ethylamino]-2H-[1,2,4]triazolo[4,3-a]pyrazin-3-one A solution of 50 mg of 6-tert-butyl-8-chloro-2H-[1,2,4]triazolo[4,3-a]pyrazin-3-one and 68 mg of 2-(6-methoxy-pyridin-3-yl)-ethylamine in THF (2 mL) was heated in a microwave apparatus (Emrys-Optimizer®, Personal Chemistry Inc., 2 Hampshire St., Suite 100, Foxboro, Mass.) at 150° C. for 10 min. The solvent was removed and the residue was purified by silica gel chromatography to afford the title compound as a white solid after trituration. MS (M+H⁺)=343.3.

The following examples were prepared in a manner analogous to that described in Example 235 using appropriate starting materials.

| Example | Name | MS (M + H)⁺ |
|---|---|---|
| 236 | 6-tert-Butyl-8-[2-(6-methyl-pyridin-3-yl)-ethylamino]-2H-[1,2,4]triazolo[4,3-a]pyrazin-3-one | 327.3 |
| 237 | 6-tert-Butyl-8-[2-(2-methyl-pyridin-3-yl)-ethylamino]-2H-[1,2,4]triazolo[4,3-a]pyrazin-3-one | 327.3 |

Biological Methodologies

GSK-3 Inhibition

The specific activities of the compounds of formula (I) in inhibiting GSK-3 can be determined in both cell-free and cell-based assays, both of which have been previously described in the relevant art. See, for example, U.S. Pat. Nos. 6,417,185 and 6,489,344, the disclosures of which are incorporated herein by reference in their entirety.

A cell-free testing assay can be generally carried out by incubating GSK-3 with a peptide substrate, radiolabeled ATP (e.g., for example, $\gamma^{33}$P- or $\gamma^{32}$P-ATP, both of which are available from Amersham; Arlington Heights, Ill.), magnesium ions, and the compound to be assayed. The mixture is incubated for a period of time to allow incorporation of radiolabeled phosphate into the peptide substrate by GSK-3 activity. The reaction mixture is then washed to remove unreacted radiolabeled ATP, typically after first transferring all or a portion of the enzyme reaction mixture to a well that contains a uniform amount of a ligand capable of binding to the peptide substrate. The amount of $\gamma^{33}P$ or $\gamma^{32}P$ remaining in each well after washing is then quantified to determine the amount of radiolabeled phosphate incorporated into the peptide substrate. Inhibition is observed as a reduction, relative to a control, in the incorporation of radiolabeled phosphate into the peptide substrate. An example of a suitable GSK-3 peptide substrate for an assay is the SGSG-linked CREB peptide sequence, described in Wang, et al., Anal. Biochem., 220, 397402 (1994). Purified GSK-3 for a testing assay may, for example, be obtained from cells transfected with a human GSK-3β expression plasmid as described in, for example, Stambolic, et al., Current Biology, 6, 1664-1668 (1996).

Another example of a GSK-3 testing assay, similar to the one described hereinabove, is as follows: enzyme activities are assayed as the incorporation of $^{33}P$ from the gamma phosphate of $^{33}P$-ATP (Amersham; Arlington Heights, Ill.; catalog #AH-9968) into biotinylated peptide substrate PKTP-KKAKKL. The reactions are carried out in a buffer containing 50 mM Tris-HCl, pH 8.0; 10 mM $MgCl_2$, 0.1 mM $Na_3VO_4$, and 1 mM DTT. The final concentration of ATP is 0.5 µM (final specific radioactivity of 4 µCi/nmol), and the final concentration of substrate is 0.75 µM. The reactions, initiated by the addition of enzyme, are carried out at room temperature for about 60 minutes. The reactions are stopped by addition of 0.6 volume of buffer containing (final concentrations): 2.5 mM EDTA, 0.05% Triton-X 100, 100 µM ATP, and 1.25 mg/ml streptavidin-coated SPA beads (Amersham; Arlington Heights, Ill.; catalog #RPNQ0007). Radioactivity associated with the beads is then quantified by standard scintillation counting.

A generally preferred GSK-3 testing assay, similar to the one described hereinabove, is as follows: enzyme activities are assayed as the incorporation of $^{33}P$ from the gamma phosphate of $^{33}P$-ATP (Amersham; Arlington Heights, Ill.; catalog #AH-9968) into biotinylated peptide substrate Biotin-SRHSSPHQpSEDEEE-OH (AnaSpec Inc., San Jose, Calif.). The reactions are carried out in a buffer containing 8 mM MOPS; 10 mM $Mg(OAc)_2$, 0.2 mM EDTA (pH 7.0), and 1 mM DTT. The final concentration of ATP is 2.0 µM (final specific radioactivity of 4 µCi/nmol), and the final concentration of substrate is 1.0 µM. The reactions, initiated by the addition of enzyme, are carried out at room temperature for about 75 minutes. The reactions are stopped by addition of 0.6 volume of buffer containing (final concentrations): 0.05 mM EDTA, 0.1% Triton-X 100, 100 µM ATP, and 2.5 mg/ml streptavidin-coated SPA beads. Radioactivity associated with the beads is then quantified by standard scintillation counting.

The compounds of formula (I) generally exhibit inhibitory activity, expressed as $IC_{50}$'s, against GSK-3 that are <10,000 nM. Generally preferred compounds have $IC_{50}$'s <200 nM. For example, the compound 6-tert-butyl-8-[2-(4-methoxy-phenoxy)-ethylamino]-2H-[1,2,4]triazolo[4,3-a]pyrazin-3-one has an $IC_{50}$ of 4.84 nM.

The invention claimed is:
1. A compound of formula (I)

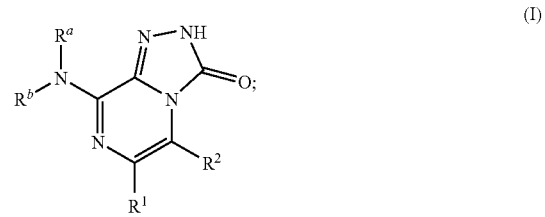

or a pharmaceutically acceptable salt thereof wherein:
$R^a$ and $R^b$ are, independently:
(1) hydrogen;
(2) acetyl;
(3) —($C_1$-$C_6$)alkyl, optionally, and independently, substituted with from one to three:
(A) cyano; (B) halogen; (C) —$NR^3R^4$; (D) —$COR^5$; (E) —$OR^6$; (F) —$SR^6$; (G) —$S(O)R^6$; (H) —$SO_2R^6$; (I) aryl, optionally substituted independently with from one to three halogen; nitro; —$SO_2NH_2$; —($C_1$-$C_6$)alkyl; methylenedioxy; —$COR^5$; or —$OR^6$; (J) heteroaryl, optionally substituted independently with from one to three hydroxy; nitro; halogen; —$OR^6$; aryl, optionally substituted independently with —($C_1$-$C_6$)alkyl; heteroaryl; trifluoromethyl; or —($C_1$-$C_6$)alkyl, optionally substituted with hydroxy; (K) —($C_3$-$C_{11}$)cycloalkyl, optionally substituted independently with from one to three cyano; —$COR^5$; or —$CH_2NR^3R^4$; or (L) —($C_3$-$C_{11}$)heterocycloalkyl, optionally substituted independently with from one to three —($C_1$-$C_6$)alkyl, optionally substituted with aryl; —$COR^5$; aryl, optionally substituted independently with halogen; oxo; or —($C_1$-$C_6$)alkoxy;
wherein:
$R^3$ and $R^4$ are independently:
(a) hydrogen; (b) —$SO^2R^6$; (c) aryl, optionally substituted independently with from one to three halogen; cyano; nitro; —($C_1$-$C_6$)alkyl, —($C_1$-$C_6$)alkoxy, or —$COR^5$; (d) —($C_1$-$C_6$)alkyl, optionally substituted independently with from one to three —($C_3$-$C_{11}$)heterocycloalkyl; —($C_3$-$C_{11}$)cycloalkyl; —($C_1$-$C_6$)alkoxy; aryl; or heteroaryl; (e) heteroaryl, optionally substituted independently with from one to three halogen; trifluoromethyl; cyano; nitro; —$COR^5$; —($C_1$-$C_6$)alkyl, optionally substituted with —($C_3$-$C_{11}$)heterocycloalkyl; or —($C_1$-$C_6$)alkoxy; (f) —($C_3$-$C_{11}$)heterocycloalkyl, optionally substituted independently with from one to three —($C_1$-$C_6$)alkyl; or (g) —$COR^5$; or
$R^3$ and $R^4$, taken together with the nitrogen atom to which they are attached, form a 5- or 6-membered heterocycloalkyl ring, optionally having from one to three additional heteroatoms independently selected from nitrogen, oxygen, and sulfur, wherein said 5- or 6-membered heterocycloalkyl ring is optionally substituted independently with from one to three —($C_1$-$C_6$)alkyl, optionally substituted with aryl;
$R^5$ is (h) hydroxy; (i) —($C_1$-$C_6$)alkyl, optionally substituted independently with from one to three —$CO_2H$; —($C_1$-$C_6$)alkoxy; or aryl; (j) —($C_1$-$C_6$)alkoxy; (k) aryl, optionally substituted with halogen; (l) heteroaryl; or (m) —($C_3$-$C_{11}$)heterocycloalkyl, optionally substituted independently with from one to three oxo; —$CO_2H$; or —($C_1$-$C_6$)alkyl; and R$^6$ is (n) hydrogen; (o) —(C$_1$-C$_6$)alkyl, optionally substituted independently with from one to three hydroxy; —(C$_1$-C$_6$)alkoxy; aryl, optionally substituted with halogen; or heteroaryl, optionally substituted with —CH$_2$NR$^3$R$^4$; (p) aryl, optionally substituted independently with from one to three halogen; —(C$_1$-C$_6$)alkyl; cyano; trifluoromethyl; or —OR$^6$; (q) heteroaryl, optionally substituted independently with from one to three amino; —(C$_1$-C$_6$)alkyl; —(C$_1$-C$_6$)alkoxy; or —COR$^5$; or (r) —(C$_3$C$_{11}$)heterocycloalkyl, optionally substituted independently with from one to three —(C$_1$-C$_6$)alkyl;

(4) —(C$_3$-C$_{11}$)cycloalkyl; or (5) —(C$_3$-C$_{11}$)heterocycloalkyl, optionally substituted independently with from one to three halogen; —COR$^5$; —(C$_1$-C$_6$)alkyl; or —(C$_1$-C$_6$)alkoxy; or R$^a$ and R$^b$, taken together with the nitrogen atom to which they are attached, form a 5- or 6-membered heterocycloalkyl ring, optionally having from one to three additional heteroatoms independently selected from the group consisting of nitrogen, oxygen, and sulfur, wherein said 5- or 6-membered heterocycloalkyl ring is optionally, and independently, substituted with from one to three halogen; —(C$_1$-C$_6$)alkyl; or heteroaryl, optionally substituted independently with from one to three halogen; trifluoromethyl; and cyano; and R$^1$ and R$^2$ are, independently, (i) hydrogen; (ii) halogen; (iii) aryl, optionally substituted independently with from one to three halogen; cyano; —(C$_1$C$_6$)alkyl; —(C$_1$-C$_6$) alkoxy; —COR$^5$; or —CONR$^3$R$^4$; (iv) —(C$_1$-C$_6$)alkyl, optionally substituted independently with from one to three aryl, optionally substituted independently with from one to three halogen or trifluoromethyl; heteroaryl; —CONR$^3$R$^4$; or hydroxy; (v) —COR$^5$; (vi) —CONR$^3$R$^4$; or (vii) —(C$_1$-C$_6$)cycloalkyl, optionally substituted independently with from one to three —COR$^5$.

2. The compound of claim 1 or a pharmaceutically acceptable salt thereof, wherein:

R$^a$ and R$^b$ are, independently:

(1) hydrogen;

(3) —(C$^1$-C$_6$)alkyl, optionally, and independently, substituted with from one to three:

(A) cyano; (B) halogen; (C) —NR$^3$R$^4$; (D) —COR$^5$; (E) —OR$^6$; (F) —SR$^6$; (G) —S(O)R$^6$; (H) —SO$_2$R$^6$; (I) aryl, optionally substituted independently with from one to three halogen; nitro; —SO$_2$NH$_2$; —(C$_1$-C$_6$)alkyl; methylenedioxy; —COR$^5$; or —OR$^6$; (J) heteroaryl, optionally substituted independently with from one to three hydroxy; nitro; halogen; —OR$^6$; aryl, optionally substituted independently with —(C$_1$-C$_6$)alkyl; heteroaryl; trifluoromethyl; or —(C$_1$-C$_6$)alkyl, optionally substituted with hydroxy; (K) —(C$_3$-C$_{11}$)cycloalkyl, optionally substituted independently with from one to three cyano; —COR$^5$; or —CH$_2$NR$^3$R$^4$; or (L) —(C$_3$-C$_{11}$)heterocycloalkyl, optionally substituted independently with from one to three —(C$_1$-C$_6$)alkyl, optionally substituted with aryl; —COR$^5$; aryl, optionally substituted independently with halogen; oxo; or —(C$_1$-C$_6$)alkoxy;

wherein:

R$^3$ and R$^4$ are independently:

(a) hydrogen; (b) —SO$_2$R$^6$; (c) aryl, optionally substituted independently with from one to three halogen; cyano; nitro; —(C$_1$-C$_6$)alkyl, —(C$_1$-C$_6$)alkoxy, or —COR$^5$; (d) —(C$_1$-C$_6$)alkyl, optionally substituted independently with from one to three —(C$_3$-C$_{11}$)heterocycloalkyl; —(C$_3$-C$_{11}$)cycloalkyl; —(C$_1$-C$_6$)alkoxy; aryl; or heteroaryl; (e) heteroaryl, optionally substituted independently with from one to three halogen; trifluoromethyl; cyano; nitro; —COR$^5$; —(C$_1$-C$_6$)alkyl, optionally substituted with —(C$_3$-C$_{11}$)heterocycloalkyl; or —(C$_1$-C$_6$) alkoxy; (f) —(C$_3$-C$_{11}$)heterocycloalkyl, optionally substituted independently with from one to three —(C$_1$-C$_6$) alkyl; or (g) —COR$^5$; or R$^3$ and R$^4$, taken together with the nitrogen atom to which they are attached, form a 5- or 6-membered heterocycloalkyl ring, optionally having from one to three additional heteroatoms independently selected from nitrogen, oxygen, and sulfur, wherein said 5- or 6-membered heterocycloalkyl ring is optionally substituted with from one to three —(C$_1$-C$_6$)alkyl, optionally substituted with aryl;

R$^5$ is (h) hydroxy; (i) —(C$_1$-C$_6$)alkyl, optionally substituted independently with from one to three —CO$_2$H; —(C$_1$-C$_6$)alkoxy; or aryl; (j) —(C$_1$-C$_6$)alkoxy; (k) aryl, optionally substituted with halogen; (l) heteroaryl; or (m) —(C$_3$-C$_{11}$)heterocycloalkyl, optionally substituted independently with from one to three oxo; —CO$_2$H; or —(C$_1$-C$_6$)alkyl; and R$^6$ is (n) hydrogen; (o) —(C$_1$-C$_6$)alkyl, optionally substituted independently with from one to three hydroxy; —(C$_1$-C$_6$)alkoxy; aryl, optionally substituted with halogen; or heteroaryl, optionally substituted with —CH$_2$NR$^3$R$^4$; (p) aryl, optionally substituted independently with from one to three halogen; —(C$_1$-C$_6$)alkyl; cyano; trifluoromethyl; or —OR$^6$; (q) heteroaryl, optionally substituted independently with from one to three amino; —(C$_1$-C$_6$)alkyl; —(C$_1$-C$_6$)alkoxy; or —COR$^5$; or (r) —(C$_3$-C$_{11}$)heterocycloalkyl, optionally substituted independently with from one to three —(C$_1$-C$_6$)alkyl;

(4) —(C$_3$-C$_{11}$)cycloalkyl; or (5) —(C$_3$-C$_{11}$)heterocycloalkyl, optionally substituted independently with from one to three halogen; —COR$^5$; —(C$_1$-C$_6$)alkyl; or —(C$_1$-C$_6$)alkoxy; and R$^1$ and R$^2$ are, independently, (ii) hydrogen; (iv) aryl, optionally substituted independently with from one to three halogen; cyano; —(C$_1$-C$_6$)alkyl; —(C$_1$-C$_6$) alkoxy; —COR$^5$; or —CONR$^3$R$^4$; or (v) —(C$_1$-C$_6$) alkyl, optionally substituted independently with from one to three aryl, optionally substituted independently with from one to three halogen or trifluoromethyl; heteroaryl; —CONR$^3$R$^4$; or hydroxy.

3. The compound of claim 1 or a pharmaceutically acceptable salt thereof, wherein:

R$^a$ and R$^b$ are, independently:

(1) hydrogen;

(3) —(C$_1$-C$_6$)alkyl, optionally, and independently, substituted with one or two:

(A) cyano; (E) —OR$^6$; (F) —SR$^6$; (I) aryl, optionally substituted with nitro; (J) heteroaryl, optionally substituted independently with one or two —OR$^6$ or —(C$_1$-C$_6$) alkyl; or (L) —(C$_3$-C$_{11}$)heterocycloalkyl, optionally substituted with oxo or —COR$^5$; wherein R$^6$is (n) hydrogen; (o) —(C$_1$-C$_6$)alkyl; (p) aryl, optionally substituted with cyano or —OR$^6$; or (q) heteroaryl, optionally substituted with amino; —(C$_1$-C$_6$)alkyl; —(C$_1$-C$_6$) alkoxy; or —COR$^5$;

(4) —(C$_3$-C$_{11}$)cycloalkyl; or (5) —(C$_3$-C$_{11}$)heterocycloalkyl, optionally substituted with —COR$^5$; wherein R$^5$ is (h) hydroxy; (i) —(C$_1$-C$_6$) alkyl; or (j) —(C$_1$-C$_6$)alkoxy; and R$^1$ and R$^2$ are, independently, hydrogen or —(C$_1$-C$_6$)alkyl.

4. A compound of claim 1 selected from the group consisting of:
- 5-[2-(6-tert-Butyl-3-oxo-2,3-dihydro-[1,2,4]triazolo[4,3-a]pyrazin-8-ylamino)-ethoxy]-nicotinic acid methyl ester;
- 8-[2-(3-aminopyridin-2-yloxy)-ethylamino]-6-tert-butyl-2H-[1,2,4]triazolo[4,3-a]pyrazin-3-one;
- 3-(6-tert-butyl-3-oxo-2,3-dihydro-[1,2,4]triazolo[4,3-a]pyrazin-8-ylamino)-propionitrile;
- 4-(6-tert-butyl-3-oxo-2,3-dihydro-[1,2,4]triazolo[4,3-a]pyrazin-8-ylamino)-piperidine-1-carboxylic acid ethyl ester;
- 3-[2-(6-tert-butyl-3-oxo-2,3-dihydro-[1,2,4]triazolo[4,3-a]pyrazin-8-ylamino)-ethoxy]-benzonitrile;
- 8-[2-(benzothiazol-2-ylamino)-ethylamino]-6-tert-butyl-2H-[1,2,4]triazolo[4,3-a]pyrazin-3-one;
- 6-tert-butyl-8-[2-(4-methoxy-phenoxy)-ethylamino]-2H-[1,2,4]triazolo[4,3-a]pyrazin-3-one;
- 6-tert-butyl-8-[2-(7-methyl-1H-benzoimidazol-2-yl)-ethyiamino]-2H-[1,2,4]triazolo[4,3-a]pyrazin-3-one;
- 6-tert-butyl-8-[2-(pyridin-3-yloxy)-ethylamino]-2H-[1,2,4]triazolo[4,3-a]pyrazin-3-one;
- 6-tert-butyl-8-[2-(pyridin-4-yloxy)-ethylamino]-2H-[1,2,4]triazolo[4,3-a]pyrazin-3-one;
- 6-tert-butyl-8-[3-(3,5-dimethyl-pyrazol-1-yl)-propylamino]-2H-[1,2,4]triazolo[4,3-a]pyrazin-3-one;
- 6-tert-butyl-8-(3-imidazol-1-yl-propylamino)-2H-[1,2,4]triazolo[4,3-a]pyrazin-3-one;
- 6-tert-butyl-8-(3-morpholin-4-yl-propylamino)-2H-[1,2,4]triazolo[4,3-a]pyrazin-3-one;
- 6-tert-butyl-8-[3-(2-oxo-pyrrolidin-1-yl)-propylamino]-2H-[1,2,4]triazolo [4,3-a]pyrazin-3-one;
- 6-tert-butyl-8-[(pyridin-3-ylmethyl)-amino]-2H-[1,2,4]triazolo[4,3-a]pyrazin-3-one;
- 6-tert-butyl-8-[(pyridin-4-ylmethyl)-amino]-2H-[1,2,4]triazolo[4,3-a]pyrazin-3-one;
- 6-tert-butyl-8-[(tetrahydro-furan-2-yl-methyl)-amino]-2H-[l,2,4]triazolo[4,3-a]pyrazin-3-one;
- 6-tert-butyl-8-(2-ethylsulfanyl-ethylamino)-2H-[1,2,4]triazolo[4,3-a]pyrazin-3-one;
- 6-tert-butyl-8-(2-hydroxy-1-methyl-ethylamino)-2H-[1,2,4]triazolo[4,3-a]pyrazin-3-one;
- 6-tert-butyl-8-(6-hydroxy-hexylamino)-2H-[1,2,4]triazolo[4,3-a]pyrazin-3-one;
- 6-tert-butyl-8-(2-methoxy-ethylamino)-2H-[1,2,4]triazolo[4,3-a]pyrazin-3-one;
- 6-tert-butyl-8-(2-pyridin-3-yl-ethylamino]-2H-[1,2,4]triazolo[4,3-a]pyrazin-3-one;
- 6-tert-butyl-8-(2-pyridin-4-yl-ethylamino]-2H-[1,2,4]triazolo[4,3-a]pyrazin-3-one;
- 6-tert-butyl-8-(4-nitro-benzylamino)-2H-[1,2,4]triazolo[4,3-a]pyrazin-3-one;
- 4-(6-tert-butyl-3-oxo-2,3-dihydro-[1,2,4]triazolo[4,3-a]pyrazin-8-ylamino)-piperidine-1-carboxylic acid ethyl ester;
- 6-tert-butyl-8-[2-(2-methyl-pyridin-3-yloxy)-ethylamino]-2H-[1,2,4]triazolo[4,3-a]pyrazin-3-one;
- 6-tert-butyl-8-[2-(2-methyl-pyridin-3-yl)-ethylamino]-2H-[1,2,4]triazolo [4,3-a]pyrazin-3-one;
- 6-tert-butyl-8-[2-(6-methoxy-pyridin-3-yl)-ethylamino]-2H-[1,2,4]triazolo[4,3-a]pyrazin-3-one;
- 6-tert-butyl-8-[2-(6-methyl-pyridin-3-yl)-ethylamino]-2H-[1,2,4]triazolo[4,3-a]pyrazin-3-one;
- 6-tert-butyl-8-(3-methoxy-propylamino)-2H-[1,2,4]triazolo[4,3-a]pyrazin-3-one;
- 6-isopropyl-5-methyl-8-(2-pyridin-3-yl-ethylamino)-2H-[1,2,4]triazolo[4,3-a]pyrazin-3-one;

or a pharmaceutically acceptable salt thereof.

5. A pharmaceutical composition comprising an amount of a compound of claim 1, or a pharmaceutically acceptable salt of said compound; and a pharmaceutically acceptable carrier, vehicle, or diluent.

* * * * *